United States Patent [19]

Komatsubara et al.

[11] Patent Number: 6,008,025
[45] Date of Patent: Dec. 28, 1999

[54] MODIFIED THERMOSTABLE DNA POLYMERASE DERIVED FROM PYROCOCCUS SP. KOD AND DNA POLYMERASE COMPOSITION THEREOF FOR NUCLEIC ACID AMPLIFICATION

[75] Inventors: Hideyuki Komatsubara; Masao Kitabayashi; Hideki Kamimura; Bunsei Kawakami; Yoshihisa Kawamura, all of Tsuruga; Masahiro Takagi; Tadayuki Imanaka, both of Suita, all of Japan

[73] Assignee: Toyo Boseki Kabushiki Kaisha, Osaka, Japan

[21] Appl. No.: 08/902,632

[22] Filed: Jul. 29, 1997

[30] Foreign Application Priority Data

Jul. 29, 1996 [JP] Japan ................................. 8-198911
Jul. 30, 1996 [JP] Japan ................................. 8-200446

[51] Int. Cl.⁶ ............................. C12P 19/34; C12N 9/12
[52] U.S. Cl. ........................................ 435/91.2; 435/194
[58] Field of Search .................... 435/194, 91.2, 435/810

[56] References Cited

U.S. PATENT DOCUMENTS 5,489,523  2/1996  Mathur ................................ 435/194
5,512,462  4/1996  Cheng ................................ 435/91.2
5,545,552  8/1996  Mathur ............................... 435/252.3
5,556,772  9/1996  Sorge et al. ........................ 435/91.2
5,602,011  2/1997  Luhm et al. ........................ 435/91.2

OTHER PUBLICATIONS

Southworth et al., Proc. Natl. Acad. Sci. USA 93, 5281–5285, 1996.
Kitabayashi et al., FASEB J. 10(6), A1245 (Abstract), 1996.
Takagi et al., App. Environ. Microbiol. 63(11), 4504–4510 1997.

*Primary Examiner*—Kenneth R. Horlick
*Attorney, Agent, or Firm*—Kenyon & Kenyon

[57] ABSTRACT

A modified thermostable DNA polymerase having 5% or less of the 3'-5' exonuclease activity of the enzyme before modification and a DNA polymerase composition for amplifying nucleic acid, which comprises the modified thermostable DNA polymerase having 0 to 5% of the 3'-5' exonuclease activity of the enzyme before modification and an unmodified thermostable DNA polymerase having 3'-5' exonuclease activity or a modified thermostable DNA polymerase having 100 to 6% of the 3'-5' exonuclease activity of a thermostable DNA polymerase before modification; a method for amplifying nucleic acid by use of said modified thermostable polymerase or said DNA polymerase composition; and a reagent therefor.

49 Claims, 7 Drawing Sheets

Lane 1 : KOD
2 : YF
3 : ND
4 : EA
5 : DEA
6 : DA
7 : Taq
M : λ/Hind I I I Marker Lane 1 : YF
2 : ND
3 : EA
4 : DEA
5 : EA
6 : Taq
7 : KOD
M : λ/Hind I I I Marker Lane 1 : ND
2 : ND+KOD
3 : Advantage Tthmix (Cloctech)
4 : Ex Taq (Takara)
5 : Taq (Toyobo)
M : λ/Hind I I I Marker

|        | EXO I       | EXO II           | EXO III      |
|--------|-------------|------------------|--------------|
| KOD    | MLAFDIETLY  | LITYNGDNFDFAYLKKR| YARYSMEDAKY  |
| Pfu    | ILAFDIETLY  | IYTYNGDSFDFPYLAKR| YAKYSMEDAKA  |
| Yeni   | LLAFDIETFY  | IITYNGDNFDLPYLIKR| YAKYSMEDAKA  |
| Deep Yeni | LLAFDIETLY | IITYNGDSFDLPYLPKP| YAKYSMEDAKY |

MODIFIED THERMOSTABLE DNA POLYMERASE DERIVED FROM PYROCOCCUS SP. KOD AND DNA POLYMERASE COMPOSITION THEREOF FOR NUCLEIC ACID AMPLIFICATION

BACKGROUND OF THE INVENTION

1. Field of the Invention

The present invention relates to a modified thermostable DNA polymerase, a DNA polymerase composition for amplifying nucleic acid, and a reagent for amplifying nucleic acid containing said enzyme or composition, as well as a method for amplifying nucleic acid by use of said reagent.

2. Description of the Related Art

Conventionally, a large number of studies have been conducted on thermostable DNA polymerases for use in techniques for amplification of nucleic acid, such as polymerase chain reaction (PCR) etc. Examples of thermostable DNA polymerases used in PCR are DNA polymerase (Tth polymerase) mostly derived from *Thermus thermophilus* and DNA polymerase (Taq polymerase) derived from *Thermus aquaticus*. Other known examples are DNA polymerases derived from a hyperthermophilic archaeon strain, such as thermostable DNA polymerase derived from *Pyrococcus furiosus* (Pfu polymerase, WO92/09689, Unexamined Published Japanese Patent Application No. 328,969/1993) and thermostable DNA polymerase derived from *Thermococcus litoralis* (Tli polymerase, Unexamined Published Japanese Patent Application No. 7160/1994).

The present inventors have previously found thermostable DNA polymerase excellent in thermostability and DNA extension rate derived from Pyrococcus sp. KOD1 (KOD polymerase, Unexamined Published Japanese Patent Application No. 298,879/1995).

However, these thermostable DNA polymerases have problems such as insufficient amplification of nucleic acid. Further problems with polymerase derived from a hyperthermophilic archaeon strain such as Pyrococcus sp. KOD1. are that it has a 3'-5' exonuclease activity and there is a limit to PCR conditions including reaction time, enzyme amount, primer concentration etc. Therefore, there is demand for novel thermostable DNA polymerase.

As a result of their eager research, the present inventors have succeeded in creating a modified enzyme derived from Pyrococcus sp. KOD1, said enzyme having the 3'-5' exonuclease activity reduced to 5% or less of the original polymerase before modification while maintaining the DNA extension rate and thermostability of the original polymerase.

The present inventors have further found that the efficiency of amplification using a polymerase before modification is improved by use of its modified thermostable DNA polymerase having a DNA extension rate of at least 30 bases/second and capable of maintaining 60% or more residual activity at pH 8.8 (determined at 25° C. because it was difficult to measure the pH at 95° C.) after treatment at 95° C. for 6 hours, said modified enzyme having the 3'-5' exonuclease activity reduced to 5% or less of the polymerase before modification, and the present inventors thereby completed the present invention.

That is, the present invention is a modified thermostable DNA polymerase having the following physicochemical properties:

action: it has a DNA polymerase activity and has 5% or less of the 3'-5' exonuclease activity of the enzyme before modification;

DNA extension rate: at least 30 bases/second; and thermostability: it is capable of maintaining 60% or more residual activity at pH 8.8 (determined at 25° C.) after treatment at 95° C. for 6 hours.

Further, the present invention is a method for amplifying nucleic acid, which comprises reacting DNA as a template, primers, dNTP and the thermostable DNA polymerase of claims 1 to 3, thus extending the primers to synthesize DNA primer extension products.

Further, the present invention is a reagent for amplifying nucleic acid, which comprises 2 kinds of primer, one of which is complementary to a DNA extension product of another primer, dNTP, said thermostable DNA polymerase, and a buffer solution.

As one of methods for amplifying long chain nucleic acid, there is a report on PCR making use of both Taq polymerase (KlenTaq-278) free of 3'-5' exonuclease activity and Pfu polymerase (or Tli polymerase) having 3'-5' exonuclease activity, or of a DNA polymerase composition containing a mixture of their mutant enzymes (Barns, W. M. (1994) Proc. Natl. Acad. Sci. USA 91, 2216–2220).

There is another report on PCR making use of a polymerase composition containing a mixture of Tth polymerase free of 3'-5' exonuclease activity, Pfu polymerase (or Tli polymerase) with 3'-5' exonuclease activity, and thermostable DNA polymerase derived from *Thermotoga maritima* (Unexamined Published Japanese Patent Application No. 38198/1996).

Higher efficiency of amplification can be attained by such a composition than by one kind of DNA polymerase but is still not sufficient because 2 kinds of DNA polymerase having different properties in thermostability and DNA extension rate are used. Hence, there has been demand for a method further excellent in efficiency of amplification.

As a result of their eager research under these circumstances, the present inventors found that PCR excellent in efficiency of amplification can be effected using a DNA polymerase composition for nucleic acid amplification, consisting of a combination of first and second DNA polymerases being almost identical to each other with respect to thermostability and DNA extension rate, the activity of the second DNA polymerase being present at a lower level than that of the first DNA polymerase, specifically a DNA polymerase composition comprising DNA polymerases selected from the group consisting of a modified thermostable DNA polymerase (first polymerase) having 0 to 5% of the 3'-5' exonuclease activity of the naturally occurring enzyme before modification and a modified thermostable DNA polymerase (second polymerase) having 100 to 6% of the 3'-5' exonuclease activity of a naturally occurring DNA polymerase or of its original naturally occurring enzyme before modification.

That is, the present invention is a DNA polymerase composition for amplifying nucleic acid, which comprises a modified thermostable DNA polymerase having 0 to 5% of the 3'-5' exonuclease activity of the original enzyme before modification (first polymerase) and the original enzyme or a modified thermostable DNA polymerase having 100 to 6% of the 3'-5' exonuclease activity of its original thermostable enzyme before modification (second polymerase), said first and second DNA polymerases having a DNA extension rate of at least 30 bases/second and capable of maintaining 60% or more residual activity at pH 8.8 (determined at 25° C.) after treatment at 95° C. for 6 hours.

Further, the present invention is a method for amplifying nucleic acid, which comprises reacting DNA as a template, primers, dNTP and said DNA polymerase composition, thus extending the primers to synthesize a DNA primer extension product.

Further, the present invention is a reagent for amplifying nucleic acid, which comprises 2 kinds of primer, one of which is complementary to a DNA extension product of another primer, dNTP, said DNA polymerase composition, divalent ions, monovalent ions, and a buffer solution.

DETAILED DESCRIPTION OF THE INVENTION

Figure 1A:
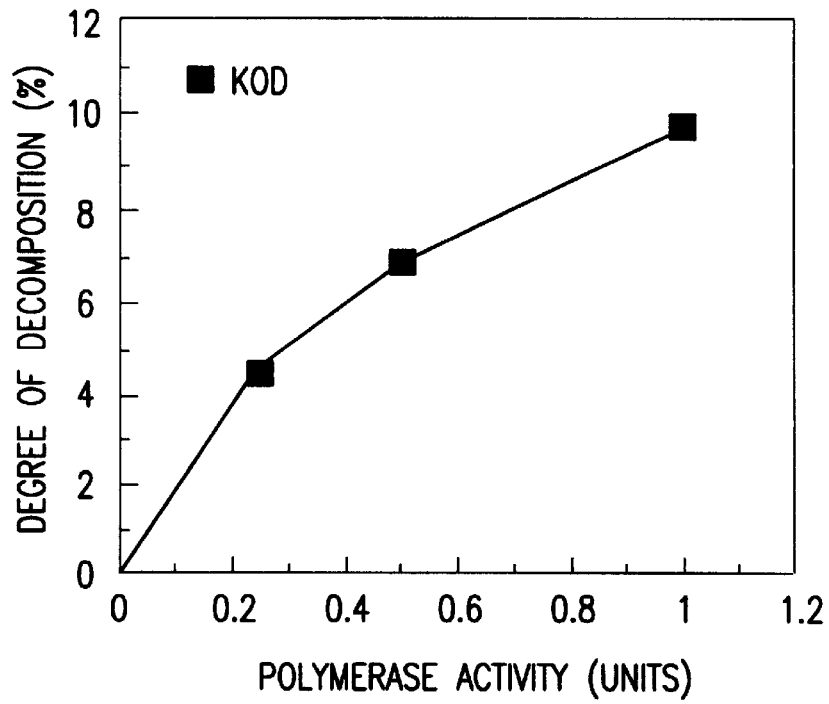
FIG. 1A shows the activity of KOD polymerase and degree of DNA decomposition.

In the present invention, DNA polymerase activity refers to a catalytic activity to introduce deoxyribonucleoside-5'-monophosphate template-dependently into deoxyribonucleic acid by covalently binding the aphosphate of deoxyribonucleoside-5'-triphosphate to the 3'-hydroxyl group of an oligonucleotide or polynucleotide annealed to a template DNA.

If the enzyme activity in a sample is high, activity measurement shall be carried out after the sample is diluted with a preserving buffer solution. In the present invention, 25 µl of Solution A below, 5 µl each of Solutions B and C below, and 10 µl of sterilized water are added to an Eppendorf tube, then stirred and mixed, and 5 µl of the above enzyme solution is added to it and reacted at 75° C. for 10 minutes. Thereafter, the sample is cooled on ice, and 50 µl of Solution E and 100 µl of Solution D below are added to it, then stirred, and cooled on ice for 10 minutes. The solution is filtered through a glass filter (Wattman GF/C Filter), and the filter is washed intensively with Solution D and ethanol, and the radioactivity of the filter is counted in a liquid scintillation counter (Packard) to determine the incorporation of the nucleotide into the template DNA. In the present invention, 1 unit of the enzyme activity shall be defined as the amount of the enzyme causing 10 nmol nucleotide per 30 minutes to be incorporated into the acid insoluble fragment under these conditions.

| | | |
|---|---|---|
| A: | 40 mM | Tris-HCl (pH 7.5) |
| | 16 mM | magnesium chloride |
| | 15 mM | dithiothreitol |
| | 100 µg/ml | BSA |
| B: | 2 µg/µl | activated calf thymus DNA |
| C: | 1.5 mM | dNTP (250 cpm/pmol [³H] dTTP) |
| D: | 20% | trichloroacetic acid |
| | | 2 mM sodium pyrophosphate) |
| E: | 1 µg/µl | carrier DNA |

In the present invention, the 3'-5' exonuclease activity refers to the activity of deleting a 3'-terminal region of DNA to deliver 5'-mononucleotide to a template.

The activity measurement method is as follows: 50 µl reaction solution (120 mM Tris-HCl (pH 8.8 at 25° C.), 10 mM KCl, 6 mM ammonium sulfate, 1 mM MgCl$_2$, 0.1% Triton X-100, 0.001% BSA, 5 µg of E. coli DNA labeled with tritium) is pipetted into a 1.5 ml Eppendorf tube, followed by adding DNA polymerase to it. After the mixture is reacted at 75° C. for 10 minutes, the reaction is terminated by cooling on ice. Then, 50 µl of 0.1% BSA is added to it as a carrier, and then 100 µl of a solution containing 10% trichloroacetic acid and 2% sodium pyrophosphate is mixed with it. After the mixture is left on ice for 15 minutes, it is centrifuged at 12,000 r.p.m. for 10 minutes to separate precipitates. 100 µl of the supernatant is measured for radioactivity in a liquid scintillation counter (Packard) whereby the amount of the nucleotide delivered to the acid soluble fragment is determined.

In the present invention, DNA extension rate refers to the number of DNAs extended per unit time. The measurement method is as follows: A reaction solution of DNA polymerase (20 mM Tris-HCl (pH 7.5), 8 mM magnesium chloride, 7.5 mM dithiothreitol, 100 µg/ml BSA, 0.1 mM dNTP, 0.2 µCi [α-$^{32}$P]dCTP) is reacted at 75° C. with a single-stranded chain of M13mp18 DNA to which a prier had been annealed. The reaction is terminated by adding an equal volume of a reaction terminating solution (50 mM sodium hydroxide, 10 mM EDTA, 5% Ficoll, 0.05 Bromophenol Blue). The DNA extended by the reaction is fractionated by electrophoresis on alkali agarose gel, and the gel is dried and subjected to autoradiography. As the DNA size marker, labeled λ/HindIII is used. The DNA extension rate is determined on the basis of the DNA size as determined with a band of this marker as an indicator.

In the present invention, thermostability means residual activity at pH 8.8 (the pH value determined at 25° C.) after treatment at 95° C. for 6 hours.

One embodiment of the present invention is a modified thermostable DNA polymerase having the following physicochemical properties:

action: it has a DNA polymerase activity and has 5% or less of the 3'-5' exonuclease activity of the original enzyme before modification, DNA extension rate: at least 30 bases/second, thermostability: it is capable of maintaining residual activity at pH 8.8 (determined at 25° C.) after treatment at 95° C. for 6 hours, optimum temperature: about 75° C., molecular weight: 88 to 90 kDa, and amino acid sequence:

an amino acid sequence as shown in SEQ ID NO: 2 in which at least one of amino acids at the 141-, 143-, 210- and 311-positions has been replaced by another amino acid.

Another embodiment of the present invention is a modified thermostable DNA polymerase having the following physicochemical properties:

action: it has a DNA polymerase activity and is free of a 3'-5' exonuclease activity, DNA extension rate: at least 30 bases/second, thermostability: it is capable of maintaining 60% or more residual activity at pH 8.8 (determined at 25° C.) after treatment at 95° C. for 6 hours, optimum temperature: about 75° C., molecular weight: 88 to 90 kDa, and amino acid sequence:

an amino acid sequence as shown in SEQ ID NO: 2 in which at least one of amino acids at the 141-, 143-, 210- and 311-positions has been replaced by another amino acid.

The thermostable DNA polymerase of the present invention before modification is an enzyme derived from Pyrococcus sp. KOD as a hyperthermophilic archaeon strain isolated in Kodakara Island, Kagoshima prefecture, Japan. The microbial properties of KOD producing this enzyme is described in Unexamined Published Japanese Patent Application No 298,879/1995. This enzyme is produced by culturing this strain.

This enzyme has the following physicochemical properties:

action: it has a DNA polymerase activity and has a 3'-5' exonuclease activity,

DNA extension rate: at least 120 bases/second, thermostability: it is capable of maintaining 60% or more residual activity at pH 8.8 (determined at 25° C.) after treatment at 95° C. for 6 hours, optimum temperature: about 75° C., molecular weight: 88 to 90 kDa, and amino acid sequence:

the amino acid sequence of SEQ ID NO: 2.

The preferable thermostable DNA polymerase of the present invention has an amino acid sequence as shown in SEQ ID NO: 2 in which at least one of amino acids at the 141-, 143-, 210- and 311-positions has been replaced by another amino acid. One example is the enzyme where in SEQ ID NO: 2 aspartic acid at the 141-position has been replaced by alanine; glutamic acid at the 143-position by alanine; aspartic acid at the 141-position and glutamic acid at the 143-position respectively by alanine; asparagine at the 210-position by aspartic acid; or tyrosine at the 311-position by phenylalanine.

For production of these modified enzymes, there is a method in which a gene coding for naturally occurring KOD polymerase is mutated so that a novel enzyme having a lower 3'-5' exonuclease activity than the naturally occurring KOD polymerase is produced by protein engineering.

Although the KOD polymerase-coding gene to be mutated is not particularly limited, a gene defined in SEQ ID NO: 3 in the Sequence Listing, derived from Pyrococcus sp. KOD, was used in one embodiment of the present invention.

A DNA polymerase gene derived from the KOD1 strain contains 2 intervening sequences (1374 to 2453 bp and 2708 to 4316 bp), and therefore a modified DNA polymerase having 3'-5' exonuclease activity reduced can be obtained by e.g. preparing with a PCR fusion method a mature gene having a nucleotide sequence as shown in SEQ ID NO: 3 from a gene as shown in SEQ ID NO: 1 and using the thus prepared gene.

In another embodiment of the present invention, a novel enzyme with a less 3'-5' activity than the naturally occurring KOD polymerase is produced by mutating a gene coding for the amino acid sequence of SEQ ID NO: 1.

To mutate the naturally occurring KOD polymerase gene, any of the known methods can be used. For example, use can be made of methods which involve bringing a drug as a mutagen into contact with the naturally occurring KOD polymerase gene or irradiating the gene with UV ray, or of protein engineering means such as the PCR technique or site specific mutagenesis. *E. coli,* whose gene undergoes mutations frequently because its mismatch repair is destroyed, can also be used for in vivo mutation.

The Chameleon™ site-directed mutagenesis kit (Stratagene) used in the present invention make use of the following steps: (1) denaturing a plasmid having a target gene inserted into it and then annealing a mutagenesis primer and a selective marker to said plasmid, (2) extending DNA by a DNA polymerase and then conducting ligation reaction using a ligase, (3) cleaving the plasmid with a restriction enzyme whose restriction site is not present in the selective primer but present in the plasmid serving as a template, whereby DNA which was not mutated is cleaved, (4) transforming *E. coli* with the remaining plasmid, (5) preparing the mutant plasmid from the transformant, followed by conducting (3) and (4) repeatedly so that the plasmid mutated as desired is obtained.

The modified polymerase gene obtained as described above is transformed into e.g. *E. coli* and then plated on a agar medium containing a drug such as ampicillin to form a colony. The colony is inoculated onto a nutrient medium such as LB medium or 2× YT medium, then cultured at 37° C. for 12 to 20 hours, and disrupted so that a crude enzyme solution is extracted from it.

To disrupt the microorganism, any of the known means by physical disruption by ultrasonication or glass beads or with lytic enzyme such as lysozyme can be used. The crude enzyme is thermally treated e.g. at 80° C. for 30 minutes to inactivate the polymerases originating in the host. Then, its DNA polymerase activity is determined and its 3'-5' exonuclease activity is determined and their activity ratio is determined. Then, this ratio is compared with that of the naturally occurring KOD polymerase in order to screen the enzyme having a reduced 3'-5' exonuclease activity.

From the strain selected in this manner, the DNA polymerase can be purified using any of the known means, for example as follows:

The microorganism cultured in a nutrient medium is recovered and disrupted enzymatically or by physical means so that a crude enzyme is extracted. The crude enzyme extract is subjected to heat treatment e.g. at 80° C. for 30 minutes and thereafter the KOD polymerase fraction is recovered by precipitation with sulfate ammonium. This crude enzyme fraction can be desalted by e.g. gel filtration on Sephadex G-25 (Pharmacia Biotech).

After this procedure, a purified enzyme preparation can be obtained by chromatography such as Q-Sepharose, heparin-Sepharose etc. In this process, the enzyme preparation can be purified to such a degree that it shows an almost single band in SDS-PAGE.

A DNA primer extension product can be produced using the modified thermostable DNA polymerase of the present invention by reacting primers and dNTP with DNA as a template to extend the primers. The primers are 2 kinds of oligonucleotide, one of which is preferably a primer complementary to a DNA extension product of another primer. Heating and cooling are carried out repeatedly.

Magnesium ions and ammonium ions and/or potassium ions are preferably coexistent for the DNA polymerase of the present invention to maintain its activity. The PCR reaction solution may further contain a buffer solution and these ions along with BSA and a nonionic surface active agent such as Triton X-100 in the buffer solution.

Because the 3'-5' exonuclease activity of the modified thermostable DNA polymerase of the present invention is reduced as compared with the enzyme before modification, PCR can be effected with higher efficiency of amplification by the modified thermostable DNA polymerase than by the enzyme before modification.

Hereinafter, the composition of at least 2 kinds of thermostable DNA polymerase which are different in their 3'-5' exonuclease activity is described.

A first DNA polymerase of the present invention is an enzyme having a 3'-5' exonuclease activity reduced to 0 to 5% preferably 1% or less of the 3'-5' exonuclease activity of the enzyme before modification.

The first DNA polymerase includes an enzyme having an amino acid sequence as shown in SEQ ID NO: 2 in which at least one of amino acids at the 141-, 142-, 143-, 210- and 311-positions has been replaced by another amino acid. One example is an enzyme having an amino acid sequence as shown in SEQ ID NO: 2 in which aspartic acid at the 141-position has been replaced by alanine; glutamic acid at the 143-position by alanine; aspartic acid at the 141-position and glutamic acid at the 143-position respectively by alanine; asparagine at the 210-position by aspartic acid; or tyrosine at the 311-position by phenylalanine. Further, it includes the enzyme where isoleucine at the 142-position has been replaced by arginine.

The first DNA polymerase of the present invention includes a modified thermostable DNA polymerase having the following physicochemical properties:

action: it has a DNA polymerase activity and has 0 to 5% of the 3'-5' exonuclease activity of the enzyme before modification;

DNA extension rate: at least 30 bases/second; and thermostability: it is capable of maintaining 60% or more residual activity at pH 8.8 (determined at 25° C.) after treatment at 95° C. for 6 hours.

The first DNA polymerase of the present invention further includes a modified thermostable DNA polymerase having the following physicochemical properties:

action: it a DNA polymerase activity and has 0 to 5% of the 3'-5' exonuclease activity of the enzyme before modification;

DNA extension rate: at least 30 bases/second;

thermostability: it is capable of maintaining residual activity at pH 8.8 (determined at 25° C.) after treatment at 95° C. for 6 hours;

optimum temperature: about 75° C.;

molecular weight: 88 to 90 kDa; and amino acid sequence:

an amino acid sequence as shown in SEQ ID NO: 2 in which at least one of amino acids at the 141-, 142-, 143-, 210- and 311-positions has been replaced by another amino acid.

The first DNA polymerase of the present invention further includes a modified thermostable DNA polymerase having the following physicochemical properties:

action: it has a DNA polymerase activity and has 0 to 5% of the 3'-5' exonuclease activity of the enzyme before modification;

DNA extension rate: at least 30 bases/second;

thermostability: it is capable of maintaining 60% or more residual activity at pH 8.8 (determined at 25° C.) after treatment at 95° C. for 6 hours;

optimum temperature: about 75° C.;

molecular weight: 88 to 90 kDa; and amino acid sequence:

an amino acid sequence as shown in SEQ ID NO: 2 in which aspartic acid at the 141-position has been replaced by alanine; isoleucine at the 142-position by arginine; glutamic acid at the 143-position by alanine; aspartic acid at the 141-position and glutamic acid at the 143-position respectively by alanine; asparagine at the 210-position by aspartic acid; or tyrosine at the 311-position by phenylalanine.

The second DNA polymerase of the present invention includes a modified thermostable polymerase having 100 to 6% preferably 90 to 30% of the 3'-5' exonuclease activity of a thermostable DNA polymerase having a 3'-5' exonuclease activity or the original unmodified thermostable DNA polymerase having a 3'-5' exonuclease activity. The second DNA polymerase includes e.g. the enzyme with the amino acid sequence of SEQ ID NO: 2 or with an amino acid sequence as shown in SEQ ID NO: 2 in which amino acids at the 140-, 142-, or 144-position have been replaced by other amino acids. One example is the enzyme with an amino acid sequence as shown in SEQ ID NO: 2 in which isoleucine at the 142-position has been replaced by aspartic acid, glutamic acid, asparagine, glutamine or lysin, or threonine at the 144-position by valine.

The second DNA polymerase of the present invention includes a modified thermostable DNA polymerase having the following physicochemical properties:

action: it has a DNA polymerase activity and has a 3'-5' exonuclease activity;

DNA extension rate: at least 30 bases/second;

thermostability: it is capable of maintaining 60% or more residual activity at pH 8.8 (determined at 25° C.) after treatment at 95° C. for 6 hours;

optimum temperature: about 75° C.;

molecular weight: 88 to 90 kDa; and amino acid sequence:

the amino acid sequence of SEQ ID NO: 2.

The second DNA polymerase of the present invention further includes a modified thermostable polymerase having the following physicochemical properties:

action: it has a DNA polymerase activity and has 100 to 6% preferably 90 to 30% of the 3'-5' exonuclease activity of the enzyme before modification;

DNA extension rate: at least 30 bases/second; and thermostability: it is capable of maintaining 60% or more residual activity at pH 8.8 (determined at 25° C.) after treatment at 95° C. for 6 hours; and amino acid sequence:

an amino acid sequence as shown in SEQ ID NO: 2 in which at least one of amino acids $X_1$, $X_2$ and $X_3$ in an $X_1DX_2EX_3$ motif present in EXO 1 has been replaced by another amino acid.

Figures 6, 7:
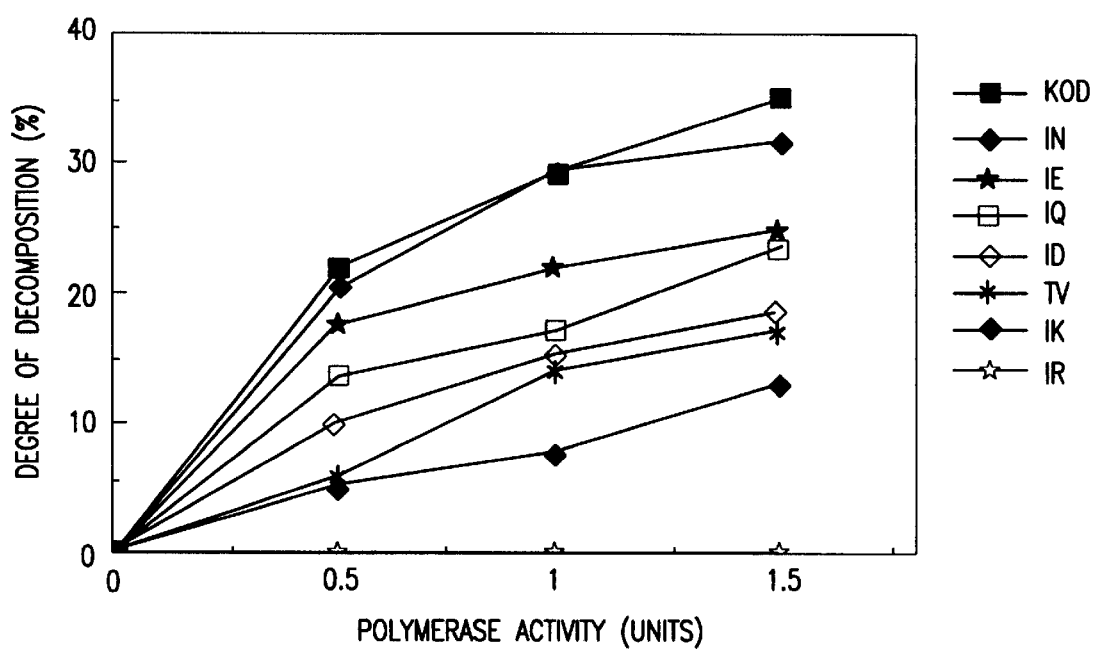
FIG. 6 shows the amino acid sequences of the exo regions of the thermostable DNA polymerase.
FIG. 7 shows the polymerase activity of the modified DNA polymerase and degree of decomposition of DNA.

In the amino acid sequence of the DNA polymerase with a 3'-5' exonuclease activity, highly preserving amino acid regions for this exonuclease activity are known (EXO I, EXO II and EXO III, FIG. 6). EXO I region contains an $X_1DX_2EX_3$ motif, and the amino acids D (aspartic acid) and E (glutamic acid) are known to be essential for the exonuclease activity.

The second DNA polymerase of the present invention further includes a modified thermostable DNA polymerase having the following physicochemical properties:

action: it has a DNA polymerase activity and has 100 to 6% preferably 90 to 30% of the 3'-5' exonuclease activity of the enzyme before modification;

DNA extension rate: at least 30 bases/second;

thermostability: it is capable of maintaining 60% or more residual activity at pH 8.8 (determined at 25° C.) after treatment at 95° C. for 6 hours; and amino acid sequence:

an amino acid sequence as shown in SEQ ID NO: 2 in which amino acids at 140-, 142-, or 144-position have been replaced by other amino acids.

The second DNA polymerase of the present invention further includes a modified thermostable DNA polymerase having the following physicochemical properties:

action: it has a DNA polymerase activity and has 100 to 6% preferably 90 to 30% of the 3'-5' exonuclease activity of the enzyme before modification;

DNA extension rate: at least 30 bases/second;

thermostability: it is capable of maintaining 60% or more residual activity at pH 8.8 (determined at 25° C.) after treatment at 95° C. for 6 hours;

optimum temperature: about 75° C.;

molecular weight: 88 to 90 KDa; and amino acid sequence:

an amino acid sequence as shown in SEQ ID NO: 2 in which is oleucine at the 142-position has been replaced by aspartic acid, glutamic acid, asparagine, glutamine or lysin, or threonine at the 144-position by valine.

The DNA extension rate of the first and second DNA polymerases is at least at least 30 bases/second, preferably 100 to 120 bases/second and they are thermostable DNA polymerases capable of maintaining 60% or more residual activity at pH 8.8 (determined at 25° C.) after treatment at 95° C. for 6 hours.

The first and second DNA polymerases are preferably KOD polymerases or their mutants.

In the present invention, the activity of the second DNA polymerase is preferably low than that of the first DNA polymerase, and the second DNA polymerase is preferably 0.02 to 0.1 unit every 2.5 units of the first DNA polymerase.

To produce these modified enzymes, there is a method in which a gene coding for e.g. naturally occurring KOD polymerase is mutated so that the novel enzymes having reduced 3'-5' exonuclease activity as compared with the naturally occurring KOD polymerase are produced by protein engineering means.

The KOD polymerase-coding gene to be mutated is not particularly limited. In one embodiment of the present invention, the gene shown in SEQ ID NO: 3 in the Sequence Listing, derived from Pyrococcus sp. KOD, was used.

In another embodiment of the present invention, a gene coding for the amino acid sequence of SEQ ID NO: 1 is mutated to produce the novel enzyme having the 3'-5' exonuclease activity reduced as compared with that of the naturally occurring KOD polymerase.

The thermostable DNA polymerase of the present invention before modification is an enzyme derived from Pyrococcus sp. KOD as 1 kind of hyperthermophilic archaeon strain isolated in Kodakara Island, Kagoshima prefecture, Japan. The microbial properties of KOD producing said enzyme are described in Unexamined Published Japanese Patent Application No 298,879/1995. Said enzyme is produced by culturing this strain.

This enzyme has the following physicochemical properties:

action: it has a DNA polymerase activity and has a 3'-5' exonuclease activity;

DNA extension rate: at least 120 bases/second;

thermostability: it is capable of maintaining 60% or more residual activity at pH 8.8 (determined at 25° C.) after treatment at 95° C. for 6 hours;

optimum temperature: about 75° C.;

molecular weight: 88 to 90 kDa; and amino acid sequence:

the amino acid sequence of SEQ ID NO: 2.

The method of amplifying nucleic acid according to the present invention comprises reacting DNA as a template, primers, and 4 kinds of deoxyribonucleotide triphosphate (dNTP) by use of said DNA polymerase composition, thus extending the primers to synthesize a DNA primer extension product.

In the PCR techniques as one method of amplifying nucleic acid according to the present invention, if a target nucleic acid in a sample is particularly long and double-stranded, then it is denatured by heating to be separated into single-stranded chains. If separation of the long chain nucleic acid into single-stranded chains is inadequate, subsequent annealing and extension reaction of the primers will be prevented. Then, the single-stranded chains as a template, primers complementary to said template, preferably primers one of which is complementary to another DNA extension product, and dNTP are reacted in a PCR reaction solution using the DNA polymerase composition of the present invention.

This reaction is carried out using a 2-stage temperature cycle, that is a high temperature stage for denaturing the nucleic acid to be amplified and a low temperature stage for annealing the primers to the denatured nucleic acid to initiate primer extension, and this cycle is repeated 25 to 40 times. Usually, 1 cycle consists of reaction at 94° C. for 0.5 to 1 minute and then at 68° C. for 0.5 to 10 minutes. The 2 primers are annealed to opposite strands of the template nucleic acid sequence, and an extension product starting at each primer is a copy complementary to the template nucleic acid, and the product is oriented so that it can hybridize to another primer when separated from the resulting double-stranded chain.

The reaction time is conducted preferably for a sufficient period until the extension reaction completes chain extension. For amplification of 20 kb or more nucleic acid, an annealing and extension time of at least 10 to 20 minutes is preferable.

A long chain nucleic acid is preferably protected from decomposition during amplification by using e.g. glycerol, dimethyl sulfoxide (DMSO) etc.

The presence of a misincorporated nucleotide will finish chain extension earlier and the number of template chains for subsequent amplification will be decreased, resulting in reduction of efficiency of amplification of long chain nucleic acid. In the present invention, however, the nucleotide misincorporated during synthesis of a primer extension product will be removed because the 3'-5' exonuclease activity besides the DNA polymerase activity is present at a low level in the reaction solution, and the dominant polymerase activity enables complete chain extension.

The pH and composition for a reaction buffer, salts (divalent and monovalent ions), and the design of primers are important for efficiency of amplification of long chain nucleic acid.

Because the PCR reagent is prepared usually at room temperature before the denaturation step, the binding of primers to another primer or to a homologous part of a nucleic acid sequence may be caused. If an extension product is also formed by nonspecific binding of primers, the efficiency of amplification of the desired long chain product is reduced. To prevent nonspecific binding, "hot start method" such as addition of the enzyme after the reaction solution reaches a high temperature is preferably used.

Divalent ions e.g. magnesium ions and monovalent ions e.g. ammonium and/or potassium ions are preferably allowed to coexist to maintain the activity of the DNA polymerase of the present invention. Further, a buffer solution, such ions, BSA, a nonionic surface active agent (e.g. Triton X-100) and buffer solution may be present in the reaction solution for nucleic acid amplification.

The reagent for amplifying nucleic acid according to the present invention contains 2 primers, one of which is complementary to a DNA extension product of another primer, dNTP, said DNA polymerase composition, magnesium ions, ammonium ions and/or potassium ions, BSA, a nonionic surface active agent and a buffer solution.

In the present invention, the activity of the second DNA polymerase is preferably lower than that of the first DNA polymerase, and it is preferable that the second DNA polymerase is present in 0.02 to 0.1 unit every 2.5 units of the first DNA polymerase.

The reagent of the present invention may contain a solvent aid such as glycerin, DMSO, polyethylene glycol etc.

The buffer solution used includes a tris buffer, tris (hydroxymethyl)methylglycine (tricine buffer), N-bis (hydroxyethyl)glycine (bicine buffer) etc. The optimum buffer solution and pH depend on the DNA polymerase used. If KOD polymerase or its mutant is used in the present invention, a buffer solution is used at pH 7.5 to 9.2 (at 25° C.) at concentration of 10 to 50 mM, preferably 20 to 120 mM. Divalent cations are preferably magnesium ions, and magnesium chloride etc. are used. Their concentration is preferably 1 to 2 mM. Monovalent cations are preferably ammonium ions or potassium ions, and ammonium sulfate, potassium glutamate, potassium acetate etc. are used. Their concentration is preferably 2 to 50 mM. The primers used are 2 kinds of oligonucleotide, one of which is a primer complementary to a DNA extension product of another primer. Their concentration is preferably 0.2 to 1 $\mu$M.

Hereinafter, the present invention is described in detail with reference to the Examples.

Reference Example 1

Cloning of DNA Polymerase Gene Derived from Hyperthermophilic Archaeon Strain KOD Hyperthermophilic archaeon strain KOD1 isolated in Kodakara Island, Kagoshima Prefecture, Japan, was cultured at 95° C. and then recovered. Genomic DNA of hyperthermophilic archaeon strain KOD was prepared in a usual manner from the microorganism. Two primers were synthesized on the basis of preserving regions in the amino acid sequence of DNA polymerase (Pfu polymerase) derived from *Pyrococcus furiosus*. PCR was conducted using the 2 primers and the genomic DNA as a template.

The DNA fragment thus amplified by PCR was sequenced, and from the nucleotide sequence thus determined, its amino acid sequence was deduced. Then, the genomic DNA from the KOD1 strain was treated with restriction enzyme, and the digest was subjected to Southern hybridization with the above amplification DNA fragment as a probe to determine the size of a fragment coding for the DNA polymerase (about 4 to 7 kbp). Further, the DNA fragment of this size was recovered from the corresponding agarose gel and inserted into plasmid pBS (Stratagene). The mixture thus obtained was transformed into *E. coli* JM109 to prepare a library. Colony hybridization with the same probe as in the Southern hybridization was conducted so that a clone strain (*E. coli* JM109/pSBKOD1) considered to contain the DNA polymerase gene derived from the KOD1 strain was obtained from the library.

Plasmid pSBKOD1 was recovered from the clone strain (*E. coli* JM109/pSBKOD1) and sequenced in a usual manner. Its amino acid sequence was deduced from the nucleotide sequence thus determined. The DNA polymerase gene derived from the KOD1 strain consisted of 5010 bases and coded for 1670. amino acids (SEQ ID NO: 1).

To prepare a complete polymerase gene, 2 intervening sequences (1374 to 2453 bp and 2708 to 4316 bp) were removed by a PCR fusion method. Three pairs of primers were used in the PCR fusion method and each pair was used in PCR where the plasmid recovered from the cloned strain was used as a template, so that 3 fragments free of the intervening sequences were amplified. The primers used in PCR were designed such that they have the same sequence as a sequence binding to the target site, and that they have different restriction enzyme sites at the terminals, that is, they have an EcoRV site at the N-terminal and a BamHI site at the C-terminal. Then, a fragment located in the middle of the PCR amplification fragment was mixed with a fragment located at the N-terminal side, and PCR was conducted using the respective fragments as primers. Further, a fragment located in the middle of the PCR amplification fragment was mixed with a fragment located at the C-terminal side, and PCR was conducted using the respective fragments as primers. PCR was conducted again using the 2 kinds of fragment thus obtained to give a complete gene fragment which is free of the intervening sequences, has an EcoRV site at the N-terminal and a BamHI site at the C-terminal, and codes for the DNA polymerase derived from the KOD1 strain. Further, this gene was subcloned in expression vector PET-8c capable of inducing expression of the gene under T7 promoter. For this subcloning, the NcoI/BamHI sites on PET-8c and the restriction enzyme sites created above were used. A recombinant expression vector (pET-pol) was thus obtained. *E. coli* BL21 (DE3)/pET-pol has been deposited as FERM BP-5513 with the National Institute of Bioscience and HumanTechnology, Agency of Industrial Science and Technology, Japan.

Example 1

Subcloning of the KOD Polymerase Gene

To modify thermostable DNA polymerase, the KOD polymerase gene was removed from plasmid pET-pol and subcloned in plasmid pBluescript as follows:

The KOD polymerase gene, about 2.3 kb long, was removed by digesting plasmid pET-pol with restriction enzymes XbaI and BamHI (Toyobo Co., Ltd.). A ligation kit (Ligation high, a product of Toyobo Co., Ltd.) was then used for ligation of this DNA fragment into plasmid pBluescript SK(-) previously digested with XbaI and BamHI. Then, the resulting plasmid was transformed into commercially available competent cells (competent high JM109, available from Toyobo Co., Ltd.).

The transformant was cultured at 35° C. for 16 hours in an LB agar medium containing 100 $\mu$g/ml ampicillin (1% Bacto-trypton, 0.5% yeast extract, 0.5% sodium chloride, 1.5% agar, produced by Gibco), and a plasmid was prepared from the resulting colonies. From its partial nucleotide sequence, this plasmid was confirmed to carry the KOD polymerase gene and it was designated plasmid pKOD1.

Example 2

Preparation of Modified Gene (DA) and Purification of Modified Thermostable DNA Polymerase Plasmid pKOD1 obtained in Example 1 was used to prepare a plasmid (PKODDA) carrying a gene for a modified thermostable DNA polymerase of the KOD polymerase of SEQ ID NO: 2 in which aspartic acid at the 141-position had been replaced by alanine.

For this preparation, a Chameleon site-directed mutagenesis kit (Stratagene) was used according to the manufacture's instructions.

The selective primer used was a primer as shown in SEQ ID NO: 4. The mutagenesis primer used was a primer as shown in SEQ ID NO: 7. The mutant was confirmed by determining its nucleotide sequence. E. coli JM109 was transformed with the resulting plasmid to give JM109 (pKODDA).

6 L sterilized TB medium (described in p. A. 2 in Molecular Cloning) containing 100 μg/ml ampicillin was introduced into a 10-L jar fermenter. Into this medium was inoculated E. coli JM109 (pKODDA) which had been cultured at 30° C. for 16 hours in 50 ml LB medium (1% Bacto-trypton, 0.5% yeast extract, 0.5% sodium chloride, produced by Gibco) containing 100 μg/ml ampicillin in a 500-ml flask, and the microorganism was grown by shake culture at 35° C. for 12 hours under aeration. The microorganism was recovered from the culture by centrifugation, then suspended in 400 ml buffer (10 mM Tris-HCl (pH 8.0), 80 mM KCl, 5 mM 2-mercaptoethanol, 1 mM EDTA) and disrupted by ultrasonication to give a cell lysate.

The cell lysate was heated at 85° C. for 30 minutes and centrifuged to remove insoluble solids. The supernatant was treated with polyethylene imine for removal of nucleic acids, then fractionated with sulfate ammonium and subjected to chromatography on heparin-Sepharose. Finally, the buffer solution was replaced by a preserving buffer solution (50 mM Tris-HCl (pH 8.0), 50 mM potassium chloride, 1 mM dithiothreitol, 0.1% Tween 20, 0.1% Nonidet™ P40, 50% glycerin) so that the modified thermostable DNA polymerase (DA) was obtained.

In the purification described above, the measurement of DNA polymerase activity was conducted in the following manner. When the enzyme activity was high, the sample was measured after dilution with the preserving buffer solution.

(Reagent)

| A: | 40 mM | Tris-HCl (pH 7.5) |
|---|---|---|
| | 16 mM | magnesium chloride |
| | 15 mM | dithiothreitol |
| | 100 μg/ml | BSA |
| B: | 2 μg/μl | activated calf thymus DNA |
| C: | 1.5 mM | dNTP (250 cpm/pmol [$^3$H] dTTP) |
| D: | 20% | trichloroacetic acid |
| | | (2 mM sodium pyrrophosphate) |
| E: | 1 μg/μl | carrier DNA |

(Method)

25 μl of Solution A, 5 μl each of Solutions B and C, and 10 μl sterilized water are added to an Eppendorf tube and mixed by stirring. Then, 5 μl of the enzyme solution is added to the mixture and reacted at 75° C. for 10 minutes. Thereafter, it is cooled on ice for 10 minutes, followed by adding 50 μl of Solution E and 100 μl of Solution D. The mixture was stirred and cooled on ice for 10 minutes. This solution is filtered through a glass filter (Wattman GF/C filter), followed by extensive washing with Solution D and ethanol, and the radioactivity of the filter was counted in a liquid scintillation counter (Packard) to determine the incorporation of the nucleotide into the template DNA.

1 unit of the enzyme is assumed to be the amount of the enzyme causing incorporation, into the acid insoluble fragment, of 10 nmol nucleotide every 30 minutes under these conditions.

Example 3

Preparation of Modified Gene (EA) and Purification of Modified Thermostable DNA Polymerase A plasmid (PKODEA) carrying a gene for a modified thermostable DNA polymerase of the KOD polymerase of SEQ ID NO: 2 in which glutamine at the 143-position had been replaced by alanine was prepared in the same manner as in Example 2.

The selective primer used was a primer as shown in SEQ ID NO: 5. The mutagenesis primer used was a primer as shown in SEQ ID NO: 8. The modified thermostable DNA polymerase (EA) was obtained using the same purification method as in Example 2.

Example 4

Preparation of Modified Gene (DEA) and Purification of Modified Thermostable DNA Polymerase A plasmid (pKODDEA) carrying a gene for a modified thermostable DNA polymerase of the KOD polymerase of SEQ ID NO: 2 in which aspartic acid at 141-position and glutamic acid at the 143-position had been replaced by alanine respectively was prepared in the same manner as in Example 2. The selective primer used was a primer as shown in SEQ ID NO: 4. The mutagenesis primer used was a primer as shown in SEQ ID NO: 6. The modified thermostable DNA polymerase (DEA) was obtained using the same purification method as in Example 2.

Example 5

Preparation of Modified Gene (ND) and Purification of Modified Thermostable DNA Polymerase A plasmid (pKODND) carrying a gene for a modified thermostable DNA polymerase of the KOD polymerase of SEQ ID NO: 2 in which asparagine at 210-position had been replaced by aspartic acid was prepared in the same manner as in Example 2. The selective primer used was a primer as shown in SEQ ID NO: 4. The mutagenesis primer used was a primer as shown in SEQ ID NO: 9. The modified thermostable DNA polymerase (ND) was obtained using the same purification method as in Example 2.

Example 6

Preparation of Modified Gene (YF) and Purification of Modified Thermostable DNA Polymerase A plasmid (pKODYF) carrying a gene for a modified thermostable DNA polymerase of the KOD polymerase of SEQ ID NO: 2 in which tyrosine at 311-position had been replaced by phenylalanine was prepared in the same manner as in Example 2. The selective primer used was a primer as shown in SEQ ID NO: 4. The mutagenesis primer used was a primer as shown in SEQ ID NO: 10. he modified thermostable DNA polymerase (YF) was obtained using the same purification method as in Example 2.

Example 7

Confirmation of Exonuclease Activity of Modified Thermostable DNA Polymerase

The exonuclease activities of the modified thermostable DNA polymerases (DA, EA, DEA, ND and YF) obtained in Examples 2 to 6 were determined in the following manner. As the control, the naturally occurring KOD polymerase (Toyobo Co., Ltd.) was used. 50 μl of a reaction solution (120 mM Tris-HCl (pH 8.8 at 25° C.), 10 mM KCl, 6 mM ammonium sulfate, 1 mM MgCl$_2$, 0.1% Triton X-100, 0.001% BSA, 5 μg tritium-labeled *E. coli* DNA) was put to a 1.5 ml Eppendorf tube, and the DNA polymerase was added in amounts of 25, 50 and 100 units respectively. The naturally occurring KOD polymerase was used in amounts of 0.25, 0.5 and 1 unit respectively. After the mixture was reacted at 75° C. for 10 minutes, the reaction was terminated by cooling on ice. Then, 50 μl of 0.1% BSA was added as a carrier to it, and then 100 μl of a solution containing 10% trichloroacetic acid and 2% sodium pyrophosphate was mixed with it. After the mixture was left for 15 minutes on ice, it is centrifuged at 12,000 r.p.m. for 10 minutes to separate the precipitates present. 100 μl of the supernatant was measured for radioactivity in a liquid scintillation counter (Packard) whereby the amount of the nucleotide delivered into the acid soluble fragment was determined.

Figure 1B:
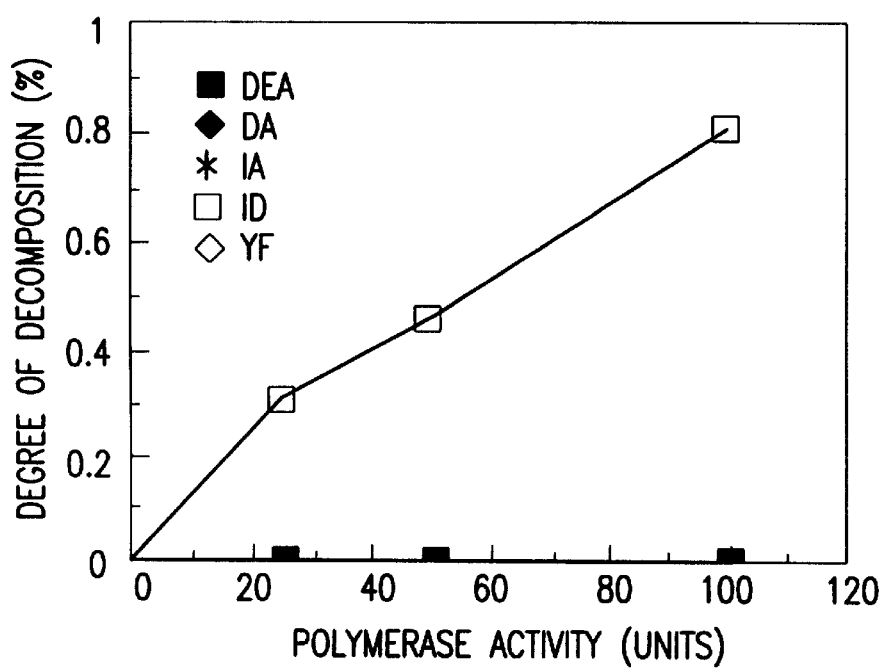
FIG. 1B shows the activity of IQ polymerase and degree of DNA decomposition.

FIG. 1 shows the polymerase activity of each DNA polymerase and the decomposition rate of DNA. In this result, the exonuclease activity of the 3 modified thermostable DNA polymerases (DEA, DA and EA) could not be detected. The modified thermostable DNA polymerase (ND) had about 0.1%, and the modified thermostable DNA polymerase (YF) had about 0.01% of the activity of the naturally occurring KOD polymerase.

Example 8

Confirmation of Thermostability

The thermostability of the modified thermostable DNA polymerases obtained in Examples 2 to 6 (DA, EA, DEA, ND and YF) was determined in the following manner. 5 units of each purified modified DNA polymerase was mixed with 100 μl buffer solution (20 mM Tris-HCl pH 8.8 at 25° C., 10 mM potassium chloride, 10 mM ammonium sulfate, 2 mM magnesium sulfate, 0.1% Triton X-100, 0.1 mg/ml BSA, 5 mM 2-mercaptoethanol) and then pre-incubated at 95° C. A sample was recovered from this mixture with time, and its polymerase activity was determined in the method described in Example 2.

Figure 2:
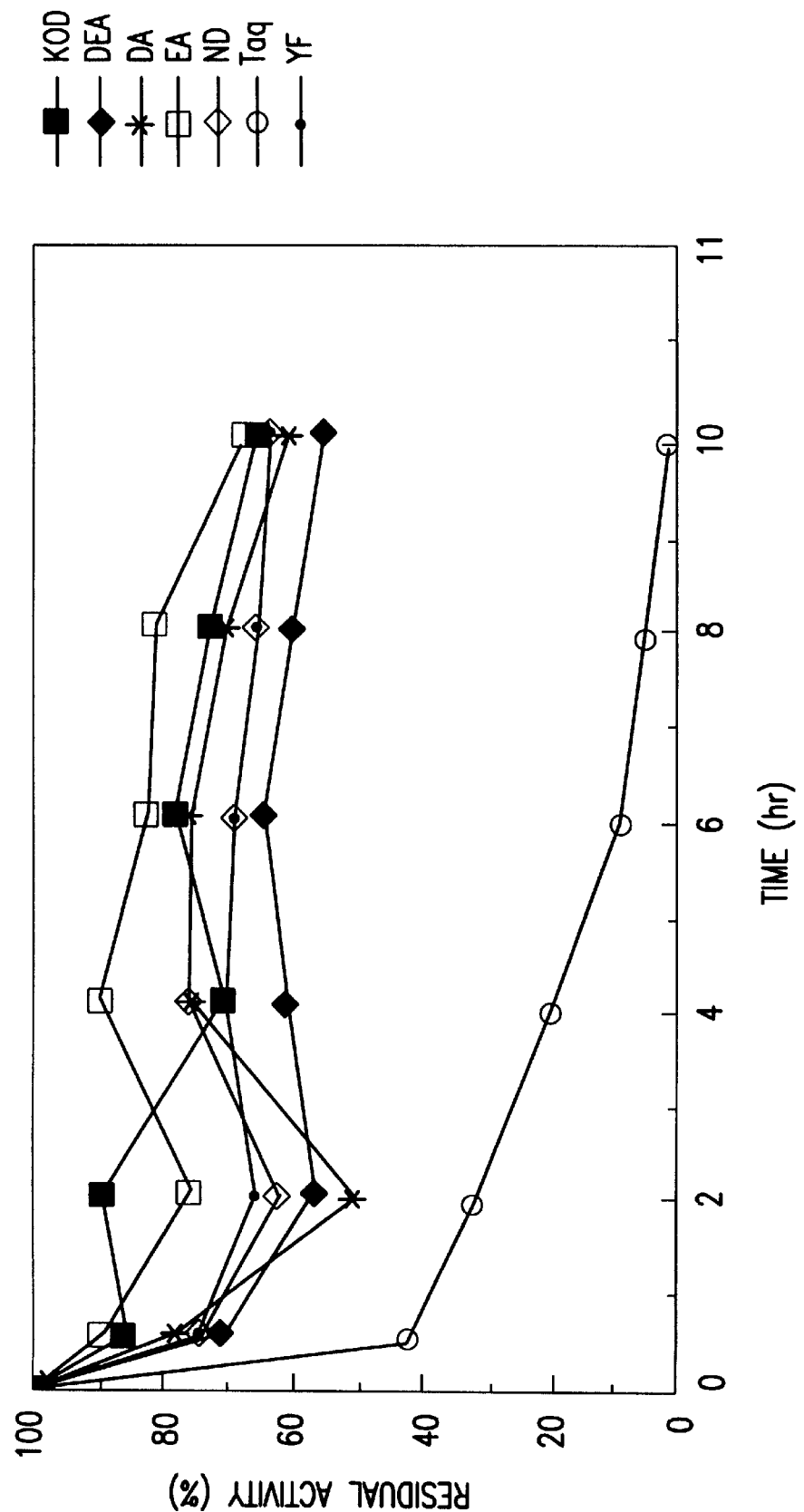
FIG. 2 shows the thermostability of the modified DNA polymerase.

For comparison, Taq polymerase (Toyobo Co., Ltd.) and the naturally occurring KOD polymerase (Toyobo Co., Ltd.) were also subjected to the same procedure. As shown in FIG. 2, any of the modified thermostable DNA polymerases, similar to the naturally occurring KOD polymerase, had 60% or more residual activity after treatment at 95° C. for 6 hours. On the other hand, Taq polymerase had 15% or less residual activity.

Example 9

Measurement of DNA Extension Rate

The modified thermostable DNA polymerases obtained in Examples 2 to 6 (DA, EA, DEA, ND and YF) was examined for DNA extension rate in the following manner. 0.2 μg of the primer (SEQ ID NO: 15) was annealed to a single-stranded chain of M13mp18 DNA, and then 1 unit of each purified modified DNA polymerase was reacted with the single-stranded chain at 75° C. for 20, 40, and 60 seconds respectively in 10 μl of a reaction solution (20 mM Tris-HCl (pH 7.5), 8 mM magnesium chloride, 7.5 mM dithiothreitol, 100 μg/ml BSA, 0.1 mM dNTP, 0.2 μCi [α-$^{32}$P]dCTP). The reaction was terminated by adding an equal volume of a reaction terminating solution (50 mM sodium hydroxide, 10 mM EDTA, 5% Ficoll, 0.05 Bromophenol Blue). For comparison, Taq polymerase (Toyobo Co., Ltd.) and the naturally occurring KOD polymerase (Toyobo Co., Ltd.) were also subjected to the same procedure.

The DNA extended by the reaction was fractionated by electrophoresis on alkali agarose gel, and the gel was dried and subjected to autoradiography. As a DNA size marker, labeled λ/HindIII was used. The DNA extension rate was determined using the size of the extended DNA determined with a band of this marker as an indicator. The result indicated that similar to the naturally occurring KOD polymerase, any of the modified polymerases had an extension rate of about 120 bases/second, while Taq polymerase had an extension rate of about 60 bases/second.

Example 10

Preparation of Mutant Gene (IN) and Purification of Modified Thermostable DNA Polymerase Plasmid pKOD1 obtained in Example 1 was used to prepare a plasmid (pKODIN) carrying a gene for modified thermostable DNA polymerase where in the $X_1X_2EX_3$ motif located in the EXO1 region, isoleucine at $X_2$ had been replaced by asparagine.

This plasmid was prepared using a Chameleon site-directed mutagenesis kit (Stratagene) according to the manufacture's instructions.

The selective primer used was a primer as shown in SEQ ID NO: 16. The mutagenesis primer used was a primer as shown in SEQ ID NO: 17. The mutant was confirmed by determining its nucleotide sequence. *E. coli* JM109 was transformed with the plasmid to give JM109 (pKODIN).

Example 11

Preparation of Mutant Gene (IE) and Purification of Modified Thermostable DNA Polymerase A thermostable polymerase gene (pKODIE) for KOD polymerase where in the $X_1DX_2EX_3$ motif located in the EXO1 region, isoleucine at $X_2$ had been replaced by glutamic acid was prepared in the same manner as in Example 10.

The selective primer used was a primer as shown in SEQ ID NO: 16. The mutagenesis primer used was a primer as shown in SEQ ID NO: 18. The modified thermostable DNA polymerase (IE) was obtained using the same purification method as in Example 10.

Example 12

Preparation of Mutant Gene (IO) and Purification of Modified Thermostable DNA Polymerase A thermostable polymerase gene (pKODIQ) for KOD polymerase where, in the $X_1DX_2EX_3$ motif located in the EXO1 region, isoleucine at $X_2$ had been replaced by glutamic acid was prepared in the same manner as in Example 10.

The selective primer used was a primer as shown in SEQ ID NO: 16. The mutagenesis primer used was a primer as shown in SEQ ID NO: 19. The modified thermostable DNA polymerase (IQ) was obtained using the same purification method as in Example 10.

Example 13

Preparation of Mutant Gene (ID) and Purification of Modified Thermostable DNA Polymerase A thermostable polymerase gene (pKODID) for KOD polymerase where, in the $X_1DX_2EX_3$ motif located in the EXO1 region, isoleucine at $X_2$ had been replaced by aspartic acid was prepared in the same manner as in Example 10.

The selective primer used was a primer as shown in SEQ ID NO: 16. The mutagenesis primer used was a primer as shown in SEQ ID NO: 20. The modified thermostable DNA polymerase (ID) was obtained using the same purification method as in Example 10.

Example 14

Preparation of Mutant Gene (TV) and Purification of Modified Thermostable DNA Polymerase A thermostable polymerase gene (pKODTV) for KOD polymerase where, in the $X_1DX_2EX_3$ motif located in the EXO1 region, tyrosine at $X_3$ had been replaced by valine was prepared in the same manner as in Example 10.

The selective primer used was a primer as shown in SEQ ID NO: 16. The mutagenesis primer used was a primer as shown in SEQ ID NO: 21. The modified thermostable DNA polymerase (TV) was obtained using the same purification method as in Example 10.

Example 15

Preparation of Mutant Gene (IK) and Purification of Modified Thermostable DNA Polymerase A thermostable polymerase gene (pKODIK) for KOD polymerase where, in the $X_1DX_2EX_3$ motif located in the EXO1 region, isoleucine at $X_2$ had been replaced by lysin was prepared in the same manner as in Example 10.

The selective primer used was a primer as shown in SEQ ID NO: 16. The mutagenesis primer used was a primer as shown in SEQ ID NO: 23. The modified thermostable DNA polymerase (IK) was obtained using the same purification method as in Example 10.

Example 16

Preparation of Mutant Gene (IR) and Purification of Modified Thermostable DNA Polymerase A thermostable polymerase gene (pKODIR) for KOD polymerase where, in the $X_1DX_2EX_3$ motif located in the EXO1 region, isoleucine at $X_2$ had been replaced by arginine was prepared in the same manner as in Example 10.

The selective primer used was a primer as shown in SEQ ID NO: 16. The mutagenesis primer used was a primer as shown in SEQ ID NO: 22. The modified thermostable DNA polymerase (IR) was obtained using the same purification method as in Example 10.

Example 17

Confirmation of Exonuclease Activity of Modified Thermostable DNA Polymerase

The modified thermostable DNA polymerases obtained in Examples 10 to 16 (IN, IE, IQ, ID, YV, IK and IR) were examined for exonuclease activity in the following manner. As the control, the naturally occurring KOD polymerase (Toyobo Co. Ltd.) was used. 50 μl of a reaction solution (120 mM Tris-HCl (pH 8.8 at 25° C.), 10 mM KCl, 6 mM ammonium sulfate, 1 MM $MgCl_2$, 0.1% Triton X-100, 0.001% BSA, 5 μg of tritium-labeled *E. coli* DNA) was pipetted into a 1.5-ml Eppendorf tube, followed by adding each DNA polymerase in amounts of 0.5, 1, and 1.5 units respectively. After the mixture was reacted at 75° C. for 10 minutes, the reaction was terminated on cooling on ice. Then, 50 ml of 0.1% BSA was added to it as a carrier, and then 100 μl of a solution containing 10% trichloroacetic acid and 2% sodium pyrrophosphate was mixed with it. After the mixture was left on ice for 15 minutes, it was centrifuged at 12,000 r.p.m. for 10 minutes to separate the precipitates present. 100 μl of the supernatant was measured for radioactivity in a liquid scintillation counter (Packard) whereby the amount of the nucleotide delivered into the acid soluble fragment was determined.

Figure 8:
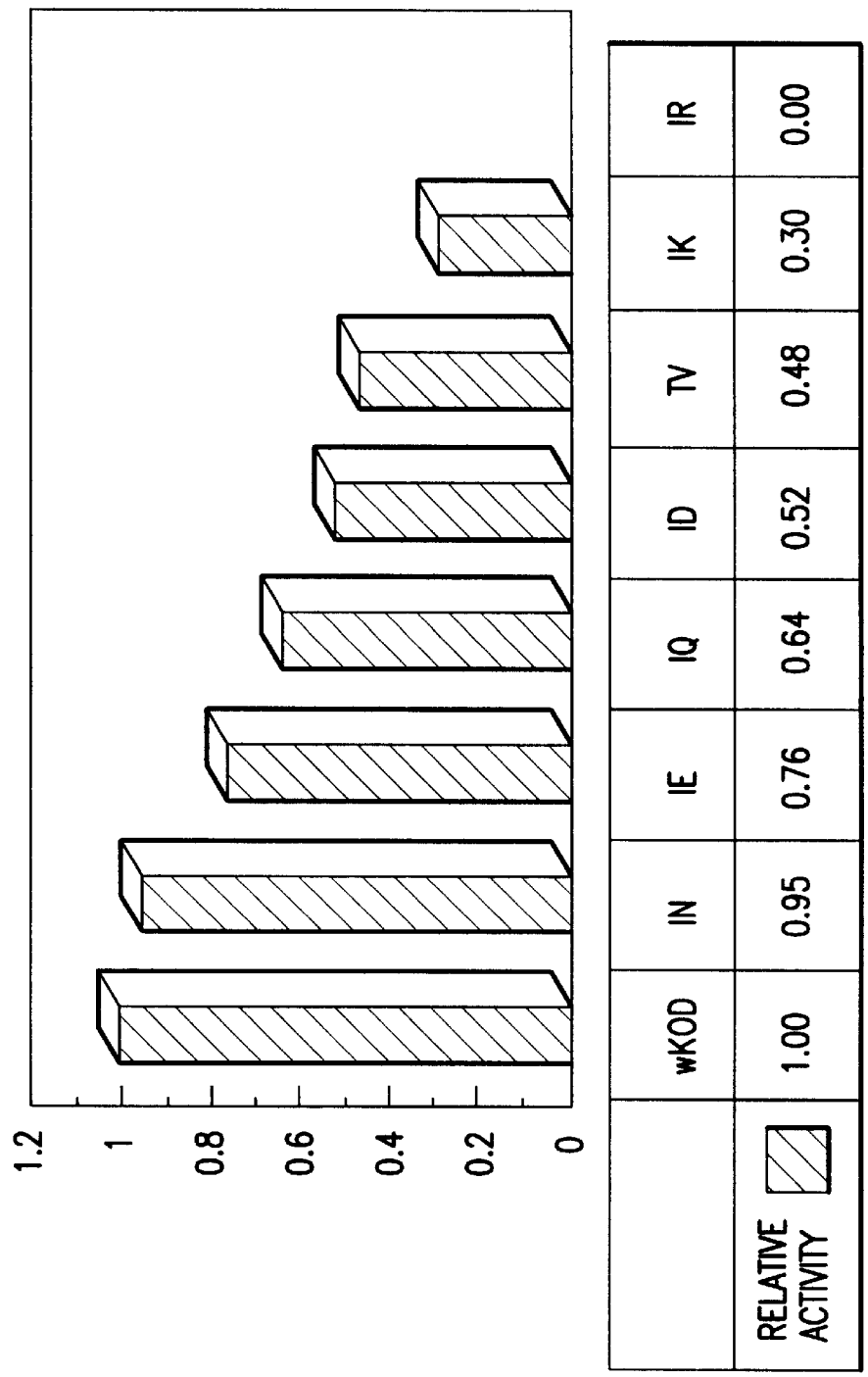
FIG. 8 shows polymerase activity relative to the naturally occurring KOD polymerase.

FIG. 7 shows the polymerase activity of each DNA polymerase and the decomposition rate of DNA. FIG. 8 shows their exonuclease activities relative to that of the naturally occurring KOD polymerase. As shown therein, the thermostable DNA polymerases with the 3'-5' exonuclease activity at different levels can be obtained according to the present invention.

As compared with the naturally occurring KOD polymerase, the modified thermostable DNA polymerases had the 3'-5' exonuclease activity at the following levels: IN had about 95%; IE, about 76%; IQ, about 64%; ID, about 52%; TV, about 48%; IK, about 30%; and IR, about 0%.

Example 18

Measurement of Fidelity of DNA Extension in PCR by Modified DNA Polymerase

The naturally occurring KOD polymerase, the modified thermostable DNA polymerases IE, ID, IK and IR, and Taq polymerase were examined for fidelity of DNA extension in PCR, as follows:

Plasmid pUR288 (described in Current Protocols in Molecular Biology 1.5.6) was cleaved with restriction enzyme ScaI. PCR was conducted using 1 ng of this plasmid and the primers of SEQ ID NOS: 13 and 14. After the reaction was finished, 5 μl of the reaction solution was subjected to agarose gel electrophoresis, and amplification of the about 5.3 kb target was confirmed. The remainder of the reaction solution was treated with phenol/chloroform and then precipitated with ethanol. The precipitate was dried and dissolved in 50 μl High buffer (50 mM Tris-HCl (pH 7.5), 100 mM NaCl, 10 mM $MgCl_2$, 1 mM DTT). Further, 10 units of restriction enzyme ScaI (Toyobo Co., Ltd.) were added to it and the mixture was reacted at 37° C. for 16 hours. The target amplification product was separated by agarose gel electrophoresis and its corresponding agarose gel was cut off from the gel. From the agarose, the target DNA was purified using Gene Clean 2 (BIO101). 10 ng of the DNA thus purified was diluted to 10 μl with TE buffer (10 mM Tris-HCl (pH 8.0), 1 mM EDTA). To this solution was added 10 μl of a reaction solution from a ligation kit (Ligation high, Toyobo Co., Ltd.), and the mixture was reacted at 16° C. for 30 minutes. Then, the resulting DNA was transformed into commercially available competent cells (competent high JM109, Toyobo K.K.).

The transformant was cultured at 35° C. for 16 hours in an LB agar medium (1% Bacto-trypton, 0.5% yeast extract, 0.5% sodium chloride, 1.5% agar, produced by Gibco) containing 100 μg/ml ampicillin, 1 mM isopropylthio-β-galactoside (IPTG, Nakarai Tesque), 0.7% 5-bromo-4-chloro-3-indolyl-β-D-galactoside (X-gal (Nakarai Tesque)) and then their colonies were counted. pUR288 carries the lacz gene (β-D-galactosidase). Therefore, if DNA extension has proceeded with fidelity during PCR, blue colonies are formed on the agar medium. On the contrary, if misincorporation has occurred during DNA extension, the activity of β-galactosidase encoded by the lacZ gene is reduced or lost, resulting in occurrence of pale blue or white colonies. Assuming these plate blue colonies and white colonies are mutant colonies, mutant frequency (%) was determined when each enzyme was used, and the results are shown in Table 1 below.

TABLE 1

|  | KOD | IE | ID | IK | IE | rTaq |
|---|---|---|---|---|---|---|
| Colonies in Total | 2394 | 3267 | 4869 | 2826 | 1197 | 2831 |
| Mutant Colonies | 19 | 63 | 148 | 362 | 299 | 795 |
| Mutant Frequency (%) | 0.79 | 1.9 | 3.0 | 12.8 | 25.0 | 28.1 |

As is evident from Table 1, the modified thermostable DNA polymerases IE, ID, IK and IR obtained in the present invention were inferior to the naturally occurring KOD polymerase, but they showed lower degrees of mutation than that of Taq polymerase, that is, they demonstrated higher fidelity in DNA extension.

Example 19

PCR by Use of Modified DNA Polymerase (for Plasmid)

PCR was carried out using naturally occurring KOD polymerase (described in Unexamined Published Japanese Patent Application No. 298,879/1995) and the modified thermostable DNA polymerase (described in Example 5), as follows: 2.5 units of each enzyme were added to 50 µl of a reaction solution (120 mM Tris-HCl (pH 8.0 at 25° C.), 10 mM KCl, 6 mM ammonium sulfate, 1 mM MgCl$_2$, 0.2 mM dNTP, 0.1% Triton X-100, 0.001% BSA, 1 ng plasmid pBR322 rendered linear with restriction enzyme ScaI, and 10 pmol primers shown in SEQ ID NOS: 13 and 14), and PCR was carried out. The thermal cycler used was Model PJ2000 (Perkin Elmer). The reaction conditions were 94° C., 30 seconds 68° C., 2.5 minutes, and this cycle was repeated 25 times. Taq polymerase (Toyobo K.K.) was subjected to PCR in the same manner except that the reaction solution was 10 mM Tris-HCl (pH 8.8 at 25° C.) containing 50 mM KCl, 1.5 mM MgCl$_2$, 0.2 mM dNTP, 0.1% Triton X-100, 1 ng plasmid pBR322 rendered linear with restriction enzyme ScaI, and 10 pmol primers shown in SEQ ID NOS: 13 and 14. After the reaction was finished, 5 µl of the reaction solution was subjected to agarose gel electrophoresis, and amplification of the about 4.3 kb target was confirmed.

Figure 3:
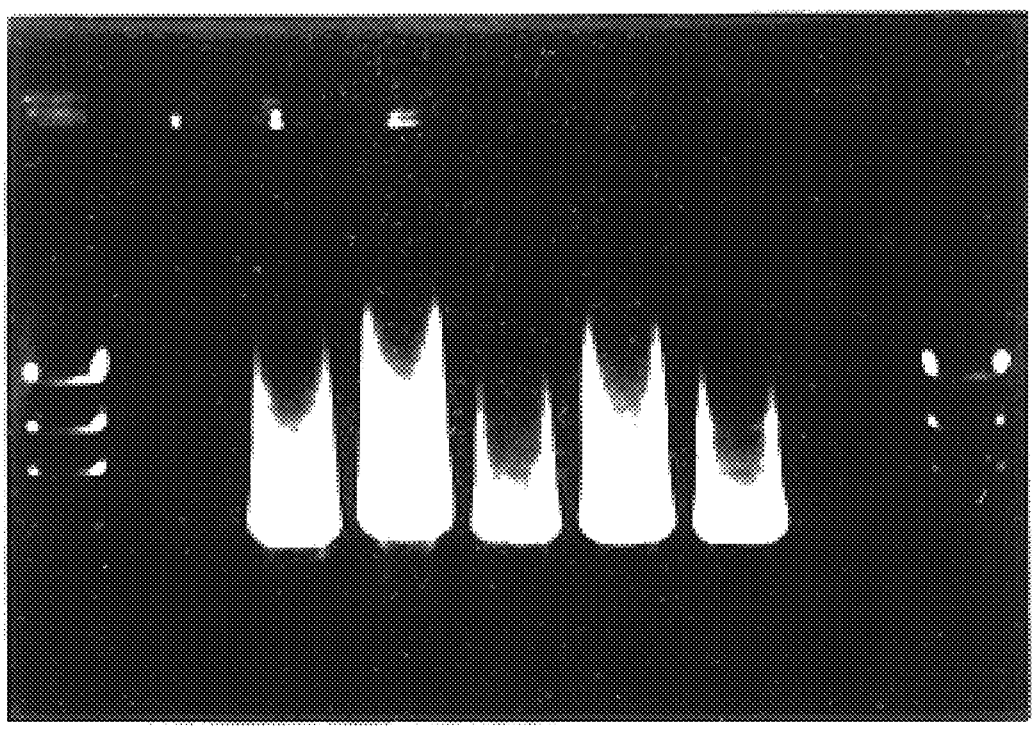
FIG. 3 shows the result of PCR by use of the modified DNA polymerase (for plasmid).

FIG. 3 shows the result of agarose gel electrophoresis. This result indicated that PCR amplification by the modified DNA polymerase was better than that by the naturally occurring KOD polymerase. Further, this amplification was better than that by Taq polymerase.

Example 20

PCR by Use of Modified DNA Polymerase (for Human Genome)

PCR was carried out using the modified thermostable DNA polymerase (described in Example 5) as follows: 2.5 units of the enzyme were added to 50 µl of a reaction solution (120 mM Tris-HCl (pH 8.0 at 25° C.), 10 mM KCl, 6 mM ammonium sulfate, 1 mM MgCl$_2$, 0.2 mM dNTP, 0.1% Triton X-100, 0.001% BSA, 100 ng genomic DNA (Clontech) derived from human placenta, and 10 pmol primers shown in SEQ ID NOS: 11 and 12), and PCR was carried out. The thermal cycler used was Model PJ2000 (Perkin Elmer). The reaction conditions were 94° C., 30 seconds 68° C., 3 minutes, and this cycle was repeated 25 times.

Figure 4:
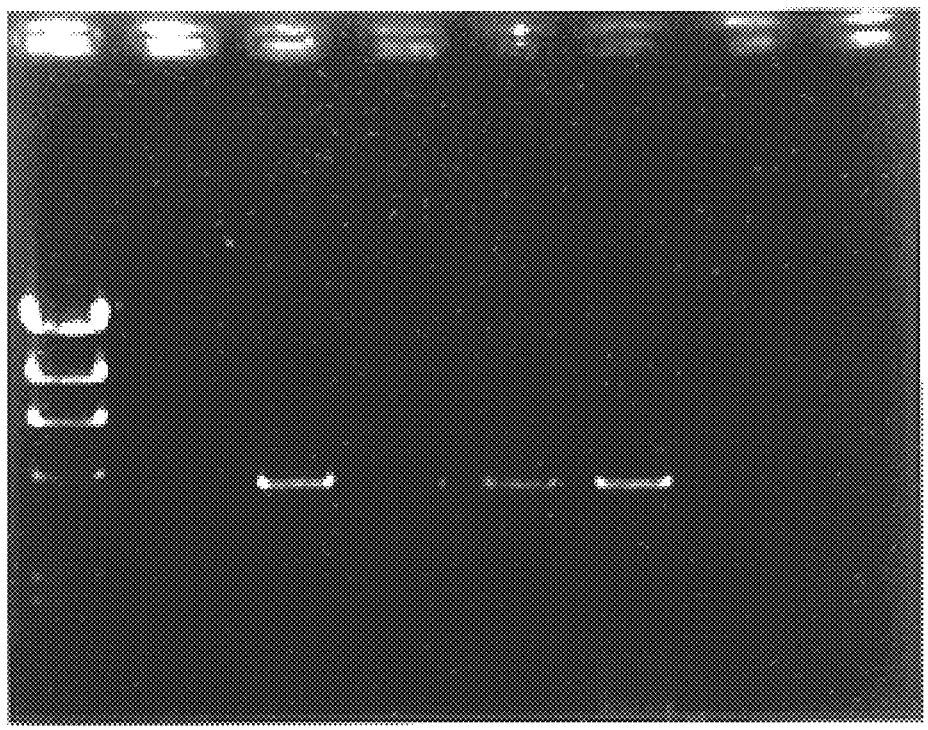
FIG. 4 shows the result of PCR by use of the modified DNA polymerase (for human genome).

For comparison, Taq polymerase (Toyobo K.K.) was also subjected to PCR in the same manner except that the reaction solution was 10 mM Tris-HCl (pH 8.8 at 25° C.) containing 50 mM KCl, 1.5 mM MgCl$_2$, 0.2 mM dNTP, 0.1% Triton X-100, 100 ng genomic DNA (Clontech) derived from human placenta, and 10 pmol primers shown in SEQ ID NOS: 11 and 12. After the reaction was finished, 5 µl of the reaction solution was subjected to agarose gel electrophoresis, and amplification of the about 4 kb target was confirmed. FIG. 4 shows the result of agarose gel electrophoresis. This result indicated that PCR amplification by the modified DNA polymerase was better than that by Taq polymerase.

Example 21

PCR by Use of DNA Polymerase Composition (for Human Genome)

PCR was carried out using a mixture of the modified thermostable DNA polymerase (DA, EA, DEA, ND or YF) and naturally occurring KOD polymerase, as follows: 2.5 units of ND and 0.05 unit of KOD polymerase were added to 50 µl of a reaction solution (120 mM Tris-HCl (pH 8.8 at 25° C.), 10 mM KCl, 6 mM ammonium sulfate, 1 mM MgCl$_2$, 0.2 mM dNTP, 0.1% Triton X-100, 0.001% BSA, 30 ng genomic DNA (Clontech) derived from human placenta, and 10 pmol primers shown in SEQ ID NOS: 11 and 12). The thermal cycler used was Model PJ2000 (Perkin Elmer). The reaction conditions were 94° C., 30 seconds → 68° C., 3 minutes, and this cycle was repeated 30 times.

Figure 5:
FIG. 5 shows the result of PCR by use of the DNA polymerase composition (for human genome).

For comparison, the modified thermostable DNA polymerase (ND), Taq polymerase (Toyobo Co., Ltd.), a commercial DNA polymerase mixture (ExTaq (Takara Shuzo Co., Ltd.), and Advantage Tth (Clontech) were subjected respectively to PCR using the same amounts of the genomic DNA and primers in the same manner except that the reaction solution was the buffer attached to the commercial product. After the reaction was finished, 5 µl of the reaction solution was subjected to agarose gel electrophoresis, and amplification of the about 4 kb target was confirmed. FIG. 5 shows the result of agarose gel electrophoresis. This result indicated that PCR amplification by a mixture of the modified DNA polymerase (ND) and the naturally occurring KOD polymerase was better than that by the commercial polymerase mixture.

Nucleic acid amplification excellent in efficiency of amplification can be effected by a mixture of 2 or more DNA polymerases which are almost identical to each other with respect to thermostability and DNA extension rate but are different in their 3'-5' exonuclease activity.

What is claimed is:

1. A modified thermostable DNA polymerase having 5% or less of the 3'-5' exonuclease activity of the thermostable DNA polymerase before modification;
   a DNA extension rate of at least 30 bases/second; being capable of maintaining 60% or more residual activity at pH 8.8, determined at 25° C., after treatment at 95° C. for 6 hours;
   exhibiting activity at an optimum temperature of about 75° C.;
   having a molecular weight of 88 to 90 kDa; and
   an amino acid sequence as shown in SEQ ID NO: 2 in which at least one of the amino acids at the 141-, 143-, 210 and 311-positions has been replaced by another amino acid.

2. A modified thermostable DNA polymerase being free of a 3'-5' exonuclease activity;
   having a DNA extension rate of at least 30 bases/second; being capable of maintaining 60% or more residual activity at pH 8.8, determined at 25° C., after treatment at 95° C. for 6 hours; exhibiting activity at an optimum temperature of about 75° C.;
   having a molecular weight of 88 to 90 kDa; and
   an amino acid sequence as shown in SEQ ID NO: 2 in which at least one of the amino acids at the 141-, 143-, 210- and 311-positions has been replaced by another amino acid.

3. The thermostable DNA polymerase according to claim 1 or 2, wherein the DNA extension rate is not less than 60 bases/second.

4. The thermostable DNA polymerase according to claim 1, wherein the 3'-5' exonuclease activity is reduced to about 1% or less.

5. The thermostable DNA polymerase according claim 1 or 2, wherein in SEQ ID NO: 2 aspartic acid at the 141-position has been replaced by another amino acid.

6. The thermostable DNA polymerase according to claim 5, wherein in SEQ ID NO: 2 aspartic acid at the 141-position has been replace by alanine.

7. The thermostable DNA polymerase according to claim 1 or 2, wherein in SEQ ID NO: 2 glutamic acid at the 143-position has been replaced by another amino acid.

8. The thermostable DNA polymerase according to claim 7, wherein in SEQ ID NO: 2 glutamic acid at the 143-position has been replaced by alanine.

9. The thermostable DNA polymerase according to claim 1 or 2, wherein in SEQ ID NO: 2 aspartic acid at the 141-position and glutamic acid at the 143-position have been replaced by other amino acids.

10. The thermostable DNA polymerase according to claim 9, wherein in SEQ ID NO: 2 aspartic acid at the 141-position and glutamic acid at the 143-position have been replaced with alanine.

11. The thermostable DNA polymerase according to claim 1 or 2, wherein in SEQ ID NO: 2 asparagine at the 210-position has been replaced by another amino acid.

12. The thermostable DNA polymerase according to claim 11, wherein in SEQ ID NO: 2 asparagine at the 210-position has been replaced by aspartic acid.

13. The thermostable DNA polymerase according to claim 1 or 2, wherein in SEQ ID NO: 2 tyrosine at the 311-position has been replaced by another amino acid.

14. The thermostable DNA polymerase according to claim 13, wherein in SEQ ID NO: 2 tyrosine at the 311-position has been replaced by phenylalanine.

15. A method for amplifying nucleic acid, which comprises reacting DNA as a template, primers, dNTP and the thermostable DNA polymerase of claim 1 or 2, thus extending the primers to synthesize a DNA primer extension product.

16. The method for amplifying nucleic acid according to claim 15, wherein the primers are 2 kinds of oligonucleotide, one of which is complementary to a DNA extension product of another primer.

17. The method for amplifying nucleic acid according to claim 15, wherein heating and cooling are repeatedly carried out.

18. A kit for amplifying nucleic acid, which comprises 2 kinds of primer, one of which is complementary to a DNA extension product of another primer, dNTP, the thermostable DNA polymerase of claim 1 or 2, and a buffer solution.

19. A kit for amplifying nucleic acid, which comprises 2 kinds of primer, one of which is complementary to a DNA extension product of another primer, dNTP, the thermostable DNA polymerase of claim 1 or 2, magnesium ions, ammonium ions and/or potassium ions, BSA, a nonionic surface active agent, and a buffer solution.

20. A DNA polymerase composition for amplifying nucleic acid, which comprises first and second thermostable DNA polymerases, said first thermostable DNA polymerase comprising a modified thermostable DNA polymerase having 0 to 5% of the 3'-5' exonuclease activity of the first thermostable DNA polymerase before modification and said second thermostable DNA polymerase comprising a thermostable DNA polymerase having 3'-5' exonuclease activity or a modified thermostable DNA polymerase having 100 to 6% of the 3'-5' exonuclease activity of the second thermostable DNA polymerase before modification, said first and second thermostable DNA polymerases having a DNA extension rate of at least 30 bases/second and being capable of maintaining 60% or more residual activity at pH 8.8, determined at 25° C., after treatment at 95° C. for 6 hours, exhibit activity at an optimum temperature of about 75° C., have molecular weights of 88 to 90 kDa, and wherein said first thermostable DNA polymerase has an amino acid sequence as shown in SEQ ID NO: 2 in which at least one of the amino acids at the 141-, 142-, 143-, 210- and 311-positions has been replaced by another amino acid and wherein said second thermostable DNA polymerase has an amino acid sequence as shown in SEQ ID NO: 2 or an amino acid sequence as shown in SEQ ID NO: 2 in which at least one of the amino acids at the 140-, 142- or 144-positions has been replaced by another amino acid.

21. The DNA polymerase composition for amplifying nucleic acid according to claim 20, wherein the DNA polymerase activity of the second thermostable DNA polymerase is lower than the DNA polymerase activity of the first thermostable DNA polymerase.

22. The DNA polymerase composition for amplifying nucleic acid according to claim 20, wherein DNA polymerase activity of the second thermostable DNA polymerase is 0.02 to 0.1 unit and the DNA polymerase activity of the first thermostable DNA polymerase is 2.5 units.

23. The DNA polymerase composition according to claim 20, wherein the 3'-5' exonuclease activity of the first modified thermostable DNA polymerase is reduced to about 1% or less of the 3'-5' exonuclease activity of the thermostable DNA polymerase before modification.

24. The DNA polymerase composition according to claim 20, wherein the first modified thermostable DNA polymerase has an amino acid sequence as shown in SEQ ID NO: 2 in which aspartic acid at the 141-position has been replaced by alanine; isoleucine at the 142-position has been replaced by arginine; glutamic acid at the 143-position has been replaced by alanine; aspartic acid at the 141-position and glutamic acid at the 143-position respectively have been replaced by alanine; asparagine at the 210-position has been replaced by aspartic acid; or tyrosine at the 311-position has been replaced by phenylalanine.

25. The DNA polymerase composition according to claim 20, wherein the first modified thermostable DNA polymerase has an amino acid sequence as shown in SEQ ID NO: 2 in which aspartic acid at the 141-position has been replaced by alanine.

26. The DNA polymerase composition according to claim 20, wherein the first modified thermostable DNA polymerase has an amino acid sequence as shown in SEQ ID NO: 2 in which isoleucine at the 142-position has been replaced by arginine.

27. The DNA polymerase composition according to claim 20, wherein the first modified thermostable DNA polymerase has an amino acid sequence as shown in SEQ ID NO: 2 in which glutamic acid at the 143-position has been replaced by alanine.

28. The DNA polymerase composition according to claim 20, wherein the first modified thermostable DNA polymerase has an amino acid sequence as shown in SEQ ID NO: 2 in which aspartic acid at the 141-position and glutamic acid at the 143-position have been replaced respectively by alanine.

29. The DNA polymerase composition according to claim 20, wherein the first modified thermostable DNA polymerase has an amino acid sequence as shown in SEQ ID NO: 2 in which asparagine at the 210-position has been replaced by aspartic acid.

30. The DNA polymerase composition according to claim 20, wherein the first modified thermostable DNA polymerase has an amino acid sequence as shown in SEQ ID NO: 2 in which tyrosine at the 311-position has been replaced by phenylalanine.

31. The DNA polymerase composition according to claim 20, wherein the second thermostable DNA polymerase has a 3'-5' exonuclease activity; and
    the amino acid sequence of SEQ ID NO: 2.

32. The DNA polymerase composition according to claim 20, wherein the second thermostable DNA polymerase is a modified thermostable DNA polymerase that has a DNA polymerase activity and has 100 to 6% of the 3'-5' exonuclease activity of the second thermostable DNA polymerase before modification; and
    an amino acid sequence as shown in SEQ ID NO: 2 in which at least one of the amino acids at the 140-, 142- or 144-positions has been replaced by another amino acid.

33. The DNA polymerase composition according to claim 20, wherein the second thermostable DNA polymerase is a modified thermostable DNA polymerase that has 100 to 6% of the 3'-5' exonuclease activity of the second thermostable DNA polymerase before modification; and
    an amino acid sequence as shown in SEQ ID NO: 2 in which isoleucine at the 142-position has been replaced by an amino acid selected from the group consisting of aspartic acid, glutamic acid, asparagine, glutamine and lysine; or threonine at the 144-position has been replaced by valine.

34. The DNA polymerase composition according to claim 20, wherein the second thermostable DNA polymerase has an amino acid sequence as shown in SEQ ID NO: 2 in which isoleucine at the 142-position has been replaced by aspartic acid.

35. The DNA polymerase composition according to claim 20, wherein the second thermostable DNA polymerase has an amino acid sequence as shown in SEQ ID NO: 2 in which isoleucine at the 142-position has been replaced by glutamic acid.

36. The DNA polymerase composition according to claim 20, wherein the second thermostable DNA polymerase has an amino acid sequence as shown in SEQ ID NO: 2 in which isoleucine at the 142-position has been replaced by asparagine.

37. The DNA polymerase composition according to claim 20, wherein the second thermostable DNA polymerase has an amino acid sequence as shown in SEQ ID NO: 2 in which isoleucine at the 142-position has been replaced by glutamine.

38. The DNA polymerase composition according to claim 20, wherein the second thermostable DNA polymerase has an amino acid sequence as shown in SEQ ID NO: 2 in which isoleucine at the 142-position has been replaced by lysine.

39. The DNA polymerase composition according to claim 20, wherein the second thermostable DNA polymerase has an amino acid sequence as shown in SEQ ID NO: 2 in which isoleucine at the 142-position has been replaced by arginine.

40. The DNA polymerase composition according to claim 20, wherein the second thermostable DNA polymerase has an amino acid sequence as shown in SEQ ID NO: 2 in which threonine at the 144-position has been replaced by valine.

41. A DNA polymerase composition for amplifying nucleic acid, which comprises first and second thermostable DNA polymerases;

the first thermostable DNA polymerase comprising a modified thermostable DNA polymerase having 0 to 5% of the 3'-5' exonuclease activity of the first thermostable DNA polymerase before modification;

a DNA extension rate of at least 30 bases/second; and an amino acid sequence as shown in SEQ ID NO: 2 in which aspartic acid at the 141-position has been replaced by alanine; isoleucine at the 142-position has been replaced by arginine; glutamic acid at the 143position has been replaced by alanine; aspartic acid at the 141-position and glutamic acid at the 143-position respectively have been replaced by alanine; asparagine at the 210-position has been replaced by aspartic acid; or tyrosine at the 311-position has been replaced by phenylalanine;

the second thermostable DNA polymerase having a 3'-5' exonuclease activity;

a DNA extension rate of at least 120 bases/second; and the amino acid sequence of SEQ ID NO: 2, or the second thermostable DNA polymerase comprises a modified thermostable DNA polymerase having 100 to 30% of the 3'-5' exonuclease activity of the second thermostable DNA polymerase before modification;

a DNA extension rate of at least 120 bases/second; and an amino acid sequence as shown in SEQ ID NO: 2 in which isoleucine at the 142-position has been replaced by an amino acid selected from the group consisting of aspartic acid, glutamic acid, asparagine, glutamine and lysine; or threonine at the 144-position has been replaced by valine and wherein each of said first and second thermostable DNA polymerases is capable of maintaining 60% or more residual activity at pH 8.8, determined at 25° C., after treatment at 95° C. for 6 hours, exhibits activity at an optimum temperature of about 75° C. and has a molecular weight of 88 to 90 kDa.

42. A DNA polymerase composition for amplifying nucleic acid, which comprises first and second thermostable DNA polymerases;

the first thermostable DNA polymerase comprising a modified thermostable DNA polymerase having 0 to 5% of the 3'-5' exonuclease activity of the first thermostable DNA polymerase before modification;

a DNA extension rate of at least 30 bases/second; and an amino acid sequence as shown in SEQ ID NO: 2 in which asparagine at the 210-position has been replaced by aspartic acid;

the second thermostable DNA polymerase having a 3'-5' exonuclease activity;

a DNA extension rate of at least 120 bases/second; and the amino acid sequence of SEQ ID NO: 2, and wherein each of said first and second thermostable DNA polymerases is capable of maintaining 60% or more residual activity at pH 8.8, determined at 25° C., after treatment at 95° C. for 6 hours, exhibits activity at an optimum temperature of about 75° C. and has a molecular weight of 88 to 90 kDa.

43. A method for amplifying nucleic acid, which comprises reacting DNA as a template, primers, dNTP and the DNA polymerase composition of claim 20 thus extending the primers to synthesize a DNA primer extension product.

44. The method for amplifying nucleic acid according to claim 43, wherein the primers are 2 kinds of oligonucleotide, one of which is complementary to a DNA extension product of another primer.

45. The method for amplifying nucleic acid according to claim 46, wherein heating and cooling are repeatedly carried out.

46. A kit for amplifying nucleic acid, which comprises the DNA polymerase composition of claim 20, divalent ions, monovalent ions, primers, dNTP, and a buffer solution.

47. A kit for amplifying nucleic acid, which comprises the DNA polymerase composition of claim 20, magnesium ions, ammonium ions and/or potassium ions, 2 kinds of primer, one of which is complementary to a DNA extension product of another primer, dNTP, BSA, a nonionic surface active agent, and a buffer solution.

48. A purified thermostable DNA polymerase having:
1) an amino acid sequence as shown in SEQ ID NO: 2 wherein isoleucine at the 142-position has been replaced by arginine;
2) DNA polymerase activity and no more than 5% of the 3'-5' exonuclease activity of an enzyme having the amino acid sequence shown in SEQ ID NO: 2;
3) a DNA extension rate of at least 30 bases per second; and
4) a molecular weight of from about 88 to about 90 kDa, wherein the thermostable DNA polymerase maintains 60% or more residual activity at pH 8.8, determined at 25° C., after treatment at 95° C. for six hours and has an optimum temperature of about 75° C.

49. A thermostable DNA polymerase according to claim 1 or 2 wherein the amino acid at position 142 is arginine.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 5342 base pairs
      (B) TYPE: nucleic acid
      (C) STRANDEDNESS: double
      (D) TOPOLOGY: linear (ii) MOLECULE TYPE: genomic DNA (vi) ORIGINAL SOURCE:
      (A) ORGANISM: hyperthermophilic archaeon
      (B) STRAIN: KOD1

(xi) SEQUENCE DESCRIPTION: SEQ ID NO:1:

```
GCTTGAGGGC CTGCGGTTAT GGGACGTTGC AGTTTGCGCC TACTCAAAGA TGCCGGTTTT         60

ATAACGGAGA AAAATGGGGA GCTATTACGA TCTCTCCTTG ATGTGGGGTT TACAATAAAG        120

CCTGGATTGT TCTACAAGAT TATGGGGGAT GAAAG ATG ATC CTC GAC ACT GAC          173
                                    Met Ile Leu Asp Thr Asp
                                                          5

TAC ATA ACC GAG GAT GGA AAG CCT GTC ATA AGA ATT TTC AAG AAG GAA         221
Tyr Ile Thr Glu Asp Gly Lys Pro Val Ile Arg Ile Phe Lys Lys Glu
            10                  15                  20

AAC GGC GAG TTT AAG ATT GAG TAC GAC CGG ACT TTT GAA CCC TAC TTC         269
Asn Gly Glu Phe Lys Ile Glu Tyr Asp Arg Thr Phe Glu Pro Tyr Phe
                25                  30                  35

TAC GCC CTC CTG AAG GAC GAT TCT GCC ATT GAG GAA GTC AAG AAG ATA         317
Tyr Ala Leu Leu Lys Asp Asp Ser Ala Ile Glu Glu Val Lys Lys Ile
        40                  45                  50

ACC GCC GAG AGG CAC GGG ACG GTT GTA ACG GTT AAG CGG GTT GAA AAG         365
Thr Ala Glu Arg His Gly Thr Val Val Thr Val Lys Arg Val Glu Lys
55                  60                  65                  70

GTT CAG AAG AAG TTC CTC GGG AGA CCA GTT GAG GTC TGG AAA CTC TAC         413
Val Gln Lys Lys Phe Leu Gly Arg Pro Val Glu Val Trp Lys Leu Tyr
                75                  80                  85

TTT ACT CAT CCG CAG GAC GTC CCA GCG ATA AGG GAC AAG ATA CGA GAG         461
Phe Thr His Pro Gln Asp Val Pro Ala Ile Arg Asp Lys Ile Arg Glu
                90                  95                 100

CAT GGA GCA GTT ATT GAC ATC TAC GAG TAC GAC ATA CCC TTC GCC AAG         509
His Gly Ala Val Ile Asp Ile Tyr Glu Tyr Asp Ile Pro Phe Ala Lys
        105                 110                 115

CGC TAC CTC ATA GAC AAG GGA TTA GTG CCA ATG GAA GGC GAC GAG GAG         557
Arg Tyr Leu Ile Asp Lys Gly Leu Val Pro Met Glu Gly Asp Glu Glu
        120                 125                 130

CTG AAA ATG CTC GCC TTC GAC ATT GAA ACT CTC TAC CAT GAG GGC GAG         605
Leu Lys Met Leu Ala Phe Asp Ile Glu Thr Leu Tyr His Glu Gly Glu
135                 140                 145                 150

GAG TTC GCC GAG GGG CCA ATC CTT ATG ATA AGC TAC GCC GAC GAG GAA         653
Glu Phe Ala Glu Gly Pro Ile Leu Met Ile Ser Tyr Ala Asp Glu Glu
                155                 160                 165

GGG GCC AGG GTG ATA ACT TGG AAG AAC GTG GAT CTC CCC TAC GTT GAC         701
Gly Ala Arg Val Ile Thr Trp Lys Asn Val Asp Leu Pro Tyr Val Asp
                170                 175                 180

GTC GTC TCG ACG GAG AGG GAG ATG ATA AAG CGC TTC CTC CGT GTT GTG         749
Val Val Ser Thr Glu Arg Glu Met Ile Lys Arg Phe Leu Arg Val Val
        185                 190                 195
```

-continued

| | | |
|---|---|---|
| AAG GAG AAA GAC CCG GAC GTT CTC ATA ACC TAC AAC GGC GAC AAC TTC<br>Lys Glu Lys Asp Pro Asp Val Leu Ile Thr Tyr Asn Gly Asp Asn Phe<br>200                           205                         210 | | 797 |
| GAC TTC GCC TAT CTG AAA AAG CGC TGT GAA AAG CTC GGA ATA AAC TTC<br>Asp Phe Ala Tyr Leu Lys Lys Arg Cys Glu Lys Leu Gly Ile Asn Phe<br>215                         220                      225                      230 | | 845 |
| GCC CTC GGA AGG GAT GGA AGC GAG CCG AAG ATT CAG AGG ATG GGC GAC<br>Ala Leu Gly Arg Asp Gly Ser Glu Pro Lys Ile Gln Arg Met Gly Asp<br>                      235                      240                      245 | | 893 |
| AGG TTT GCC GTC GAA GTG AAG GGA CGG ATA CAC TTC GAT CTC TAT CCT<br>Arg Phe Ala Val Glu Val Lys Gly Arg Ile His Phe Asp Leu Tyr Pro<br>              250                      255                      260 | | 941 |
| GTG ATA AGA CGG ACG ATA AAC CTG CCC ACA TAC ACG CTT GAG GCC GTT<br>Val Ile Arg Arg Thr Ile Asn Leu Pro Thr Tyr Thr Leu Glu Ala Val<br>        265                      270                      275 | | 989 |
| TAT GAA GCC GTC TTC GGT CAG CCG AAG GAG AAG GTT TAC GCT GAG GAA<br>Tyr Glu Ala Val Phe Gly Gln Pro Lys Glu Lys Val Tyr Ala Glu Glu<br>280                         285                      290 | | 1037 |
| ATA ACA CCA GCC TGG GAA ACC GGC GAG AAC CTT GAG AGA GTC GCC CGC<br>Ile Thr Pro Ala Trp Glu Thr Gly Glu Asn Leu Glu Arg Val Ala Arg<br>295                         300                      305                      310 | | 1085 |
| TAC TCG ATG GAA GAT GCG AAG GTC ACA TAC GAG CTT GGG AAG GAG TTC<br>Tyr Ser Met Glu Asp Ala Lys Val Thr Tyr Glu Leu Gly Lys Glu Phe<br>                      315                      320                      325 | | 1133 |
| CTT CCG ATG GAG GCC CAG CTT TCT CGC TTA ATC GGC CAG TCC CTC TGG<br>Leu Pro Met Glu Ala Gln Leu Ser Arg Leu Ile Gly Gln Ser Leu Trp<br>              330                      335                      340 | | 1181 |
| GAC GTC TCC CGC TCC AGC ACT GGC AAC CTC GTT GAG TGG TTC CTC CTC<br>Asp Val Ser Arg Ser Ser Thr Gly Asn Leu Val Glu Trp Phe Leu Leu<br>        345                      350                      355 | | 1229 |
| AGG AAG GCC TAT GAG AGG AAT GAG CTG GCC CCG AAC AAG CCC GAT GAA<br>Arg Lys Ala Tyr Glu Arg Asn Glu Leu Ala Pro Asn Lys Pro Asp Glu<br>360                         365                      370 | | 1277 |
| AAG GAG CTG GCC AGA AGA CGG CAG AGC TAT GAA GGA GGC TAT GTA AAA<br>Lys Glu Leu Ala Arg Arg Arg Gln Ser Tyr Glu Gly Gly Tyr Val Lys<br>375                         380                      385                      390 | | 1325 |
| GAG CCC GAG AGA GGG TTG TGG GAG AAC ATA GTG TAC CTA GAT TTT AGA<br>Glu Pro Glu Arg Gly Leu Trp Glu Asn Ile Val Tyr Leu Asp Phe Arg<br>                      395                      400                      405 | | 1373 |
| TGC CAT CCA GCC GAT ACG AAG GTT GTC GTC AAG GGG AAG GGG ATT ATA<br>Cys His Pro Ala Asp Thr Lys Val Val Val Lys Gly Lys Gly Ile Ile<br>              410                      415                      420 | | 1421 |
| AAC ATC AGC GAG GTT CAG GAA GGT GAC TAT GTC CTT GGG ATT GAC GGC<br>Asn Ile Ser Glu Val Gln Glu Gly Asp Tyr Val Leu Gly Ile Asp Gly<br>        425                      430                      435 | | 1469 |
| TGG CAG AGA GTT AGA AAA GTA TGG GAA TAC GAC TAC AAA GGG GAG CTT<br>Trp Gln Arg Val Arg Lys Val Trp Glu Tyr Asp Tyr Lys Gly Glu Leu<br>440                         445                      450 | | 1517 |
| GTA AAC ATA AAC GGG TTA AAG TGT ACG CCC AAT CAT AAG CTT CCC GTT<br>Val Asn Ile Asn Gly Leu Lys Cys Thr Pro Asn His Lys Leu Pro Val<br>455                         460                      465                      470 | | 1565 |
| GTT ACA AAG AAC GAA CGA CAA ACG AGA ATA AGA GAC AGT CTT GCT AAG<br>Val Thr Lys Asn Glu Arg Gln Thr Arg Ile Arg Asp Ser Leu Ala Lys<br>                      475                      480                      485 | | 1613 |
| TCT TTC CTT ACT AAA AAA GTT AAG GGC AAG ATA ATA ACC ACT CCC CTT<br>Ser Phe Leu Thr Lys Lys Val Lys Gly Lys Ile Ile Thr Thr Pro Leu<br>              490                      495                      500 | | 1661 |
| TTC TAT GAA ATA GGC AGA GCG ACA AGT GAG AAT ATT CCA GAA GAA GAG<br>Phe Tyr Glu Ile Gly Arg Ala Thr Ser Glu Asn Ile Pro Glu Glu Glu<br>        505                      510                      515 | | 1709 |

```
GTT CTC AAG GGA GAG CTC GCT GGC ATA CTA TTG GCT GAA GGA ACG CTC      1757
Val Leu Lys Gly Glu Leu Ala Gly Ile Leu Leu Ala Glu Gly Thr Leu
        520                 525                 530

TTG AGG AAA GAC GTT GAA TAC TTT GAT TCA TCC CGC AAA AAA CGG AGG      1805
Leu Arg Lys Asp Val Glu Tyr Phe Asp Ser Ser Arg Lys Lys Arg Arg
535                 540                 545                 550

ATT TCA CAC CAG TAT CGT GTT GAG ATA ACC ATT GGG AAA GAC GAG GAG      1853
Ile Ser His Gln Tyr Arg Val Glu Ile Thr Ile Gly Lys Asp Glu Glu
                555                 560                 565

GAG TTT AGG GAT CGT ATC ACA TAC ATT TTT GAG CGT TTG TTT GGG ATT      1901
Glu Phe Arg Asp Arg Ile Thr Tyr Ile Phe Glu Arg Leu Phe Gly Ile
            570                 575                 580

ACT CCA AGC ATC TCG GAG AAG AAA GGA ACT AAC GCA GTA ACA CTC AAA      1949
Thr Pro Ser Ile Ser Glu Lys Lys Gly Thr Asn Ala Val Thr Leu Lys
        585                 590                 595

GTT GCG AAG AAG AAT GTT TAT CTT AAA GTC AAG GAA ATT ATG GAC AAC      1997
Val Ala Lys Lys Asn Val Tyr Leu Lys Val Lys Glu Ile Met Asp Asn
600                 605                 610

ATA GAG TCC CTA CAT GCC CCC TCG GTT CTC AGG GGA TTC TTC GAA GGC      2045
Ile Glu Ser Leu His Ala Pro Ser Val Leu Arg Gly Phe Phe Glu Gly
615                 620                 625                 630

GAC GGT TCA GTA AAC AGG GTT AGG AGG AGT ATT GTT GCA ACC CAG GGT      2093
Asp Gly Ser Val Asn Arg Val Arg Arg Ser Ile Val Ala Thr Gln Gly
                635                 640                 645

ACA AAG AAC GAG TGG AAG ATT AAA CTG GTG TCA AAA CTG CTC TCC CAG      2141
Thr Lys Asn Glu Trp Lys Ile Lys Leu Val Ser Lys Leu Leu Ser Gln
            650                 655                 660

CTT GGT ATC CCT CAT CAA ACG TAC ACG TAT CAG TAT CAG GAA AAT GGG      2189
Leu Gly Ile Pro His Gln Thr Tyr Thr Tyr Gln Tyr Gln Glu Asn Gly
        665                 670                 675

AAA GAT CGG AGC AGG TAT ATA CTG GAG ATA ACT GGA AAG GAC GGA TTG      2237
Lys Asp Arg Ser Arg Tyr Ile Leu Glu Ile Thr Gly Lys Asp Gly Leu
680                 685                 690

ATA CTG TTC CAA ACA CTC ATT GGA TTC ATC AGT GAA AGA AAG AAC GCT      2285
Ile Leu Phe Gln Thr Leu Ile Gly Phe Ile Ser Glu Arg Lys Asn Ala
695                 700                 705                 710

CTG CTT AAT AAG GCA ATA TCT CAG AGG GAA ATG AAC AAC TTG GAA AAC      2333
Leu Leu Asn Lys Ala Ile Ser Gln Arg Glu Met Asn Asn Leu Glu Asn
                715                 720                 725

AAT GGA TTT TAC AGG CTC AGT GAA TTC AAT GTC AGC ACG GAA TAC TAT      2381
Asn Gly Phe Tyr Arg Leu Ser Glu Phe Asn Val Ser Thr Glu Tyr Tyr
            730                 735                 740

GAG GGC AAG GTC TAT GAC TTA ACT CTT GAA GGA ACT CCC TAC TAC TTT      2429
Glu Gly Lys Val Tyr Asp Leu Thr Leu Glu Gly Thr Pro Tyr Tyr Phe
        745                 750                 755

GCC AAT GGC ATA TTG ACC CAT AAC TCC CTG TAC CCC TCA ATC ATC ATC      2477
Ala Asn Gly Ile Leu Thr His Asn Ser Leu Tyr Pro Ser Ile Ile Ile
760                 765                 770

ACC CAC AAC GTC TCG CCG GAT ACG CTC AAC AGA GAA GGA TGC AAG GAA      2525
Thr His Asn Val Ser Pro Asp Thr Leu Asn Arg Glu Gly Cys Lys Glu
775                 780                 785                 790

TAT GAC GTT GCC CCA CAG GTC GGC CAC CGC TTC TGC AAG GAC TTC CCA      2573
Tyr Asp Val Ala Pro Gln Val Gly His Arg Phe Cys Lys Asp Phe Pro
                795                 800                 805

GGA TTT ATC CCG AGC CTG CTT GGA GAC CTC CTA GAG GAG AGG CAG AAG      2621
Gly Phe Ile Pro Ser Leu Leu Gly Asp Leu Leu Glu Glu Arg Gln Lys
            810                 815                 820

ATA AAG AAG AAG ATG AAG GCC ACG ATT GAC CCG ATC GAG AGG AAG CTC      2669
Ile Lys Lys Lys Met Lys Ala Thr Ile Asp Pro Ile Glu Arg Lys Leu
        825                 830                 835
```

-continued

| | | |
|---|---|---|
| CTC GAT TAC AGG CAG AGG GCC ATC AAG ATC CTG GCA AAC AGC ATC CTA<br>Leu Asp Tyr Arg Gln Arg Ala Ile Lys Ile Leu Ala Asn Ser Ile Leu<br>840                               845                            850 | | 2717 |
| CCC GAG GAA TGG CTT CCA GTC CTC GAG GAA GGG GAG GTT CAC TTC GTC<br>Pro Glu Glu Trp Leu Pro Val Leu Glu Glu Gly Glu Val His Phe Val<br>855                               860                            865                            870 | | 2765 |
| AGG ATT GGA GAG CTC ATA GAC CGG ATG ATG GAG GAA AAT GCT GGG AAA<br>Arg Ile Gly Glu Leu Ile Asp Arg Met Met Glu Glu Asn Ala Gly Lys<br>                           875                             880                            885 | | 2813 |
| GTA AAG AGA GAG GGC GAG ACG GAA GTG CTT GAG GTC AGT GGG CTT GAA<br>Val Lys Arg Glu Gly Glu Thr Glu Val Leu Glu Val Ser Gly Leu Glu<br>                     890                             895                             900 | | 2861 |
| GTC CCG TCC TTT AAC AGG AGA ACT AAC AAG GCC GAG CTC AAG AGA GTA<br>Val Pro Ser Phe Asn Arg Arg Thr Asn Lyn Ala Glu Leu Lys Arg Val<br>905                               910                               915 | | 2909 |
| AAG GCC CTG ATT AGG CAC GAT TAT TCT GGC AAG GTC TAC ACC ATC AGA<br>Lys Ala Leu Ile Arg His Asp Tyr Ser Gly Lys Val Tyr Thr Ile Arg<br>920                               925                             930 | | 2957 |
| CTG AAG TCG GGG AGG AGA ATA AAG ATA ACC TCT GGC CAC AGC CTC TTC<br>Leu Lys Ser Gly Arg Arg Ile Lys Ile Thr Ser Gly His Ser Leu Phe<br>935                               940                             945                            950 | | 3005 |
| TCT GTG AGA AAC GGG GAG CTC GTT GAA GTT ACG GGC GAT GAA CTA AAG<br>Ser Val Arg Asn Gly Glu Leu Val Glu Val Thr Gly Asp Glu Leu Lys<br>                         955                             960                            965 | | 3053 |
| CCA GGT GAC CTC GTT GCA GTC CCG CGG AGA TTG GAG CTT CCT GAG AGA<br>Pro Gly Asp Leu Val Ala Val Pro Arg Arg Leu Glu Leu Pro Glu Arg<br>                   970                             975                             980 | | 3101 |
| AAC CAC GTG CTG AAC CTC GTT GAA CTG CTC CTT GGA ACG CCA GAA GAA<br>Asn His Val Leu Asn Leu Val Glu Leu Leu Leu Gly Thr Pro Glu Glu<br>                         985                             990                            995 | | 3149 |
| GAA ACT TTG GAC ATC GTC ATG ACG ATC CCA GTC AAG GGT AAG AAG AAC<br>Glu Thr Leu Asp Ile Val Met Thr Ile Pro Val Lys Gly Lys Lys Asn<br>1000                           1005                           1010 | | 3197 |
| TTC TTT AAA GGG ATG CTC AGG ACT TTG CGC TGG ATT TTC GGA GAG GAA<br>Phe Phe Lys Gly Met Leu Arg Thr Leu Arg Trp Ile Phe Gly Glu Glu<br>1015                           1020                           1025                           1030 | | 3245 |
| AAG AGG CCC AGA ACC GCG AGA CGC TAT CTC AGG CAC CTT GAG GAT CTG<br>Lys Arg Pro Arg Thr Ala Arg Arg Tyr Leu Arg His Leu Glu Asp Leu<br>                         1035                           1040                           1045 | | 3293 |
| GGC TAT GTC CGG CTT AAG AAG ATC GGC TAC GAA GTC CTC GAC TGG GAC<br>Gly Tyr Val Arg Leu Lys Lys Ile Gly Tyr Glu Val Leu Asp Trp Asp<br>                     1050                           1055                           1060 | | 3341 |
| TCA CTT AAG AAC TAC AGA AGG CTC TAC GAG GCG CTT GTC GAG AAC GTC<br>Ser Leu Lys Asn Tyr Arg Arg Leu Tyr Glu Ala Leu Val Glu Asn Val<br>                  1065                           1070                           1075 | | 3389 |
| AGA TAC AAC GGC AAC AAG AGG GAG TAC CTC GTT GAA TTC AAT TCC ATC<br>Arg Tyr Asn Gly Asn Lys Arg Glu Tyr Leu Val Glu Phe Asn Ser Ile<br>1080                           1085                           1090 | | 3437 |
| CGG GAT GCA GTT GGC ATA ATG CCC CTA AAA GAG CTG AAG GAG TGG AAG<br>Arg Asp Ala Val Gly Ile Met Pro Leu Lys Glu Leu Lys Glu Trp Lys<br>1095                           1100                           1105                           1110 | | 3485 |
| ATC GGC ACG CTG AAC GGC TTC AGA ATG AGA AAG CTC ATT GAA GTG GAC<br>Ile Gly Thr Leu Asn Gly Phe Arg Met Arg Lys Leu Ile Glu Val Asp<br>                  1115                           1120                           1125 | | 3533 |
| GAG TCG TTA GCA AAG CTC CTC GGC TAC TAC GTG AGC GAG GGC TAT GCA<br>Glu Ser Leu Ala Lys Leu Leu Gly Tyr Tyr Val Ser Glu Gly Tyr Ala<br>                  1130                           1135                           1140 | | 3581 |
| AGA AAG CAG AGG AAT CCC AAA AAC GGC TGG AGC TAC AGC GTG AAG CTC<br>Arg Lys Gln Arg Asn Pro Lys Asn Gly Trp Ser Tyr Ser Val Lys Leu<br>1145                           1150                           1155 | | 3629 |

-continued

| | | |
|---|---|---|
| TAC AAC GAA GAC CCT GAA GTG CTG GAC GAT ATG GAG AGA CTC GCC AGC<br>Tyr Asn Glu Asp Pro Glu Val Leu Asp Asp Met Glu Arg Leu Ala Ser<br>1160                     1165                   1170 | 3677 |
| AGG TTT TTC GGG AAG GTG AGG CGG GGC AGG AAC TAC GTT GAG ATA CCG<br>Arg Phe Phe Gly Lys Val Arg Arg Gly Arg Asn Tyr Val Glu Ile Pro<br>1175                     1180                   1185                   1190 | 3725 |
| AAG AAG ATC GGC TAC CTG CTC TTT GAG AAC ATG TGC GGT GTC CTA GCG<br>Lys Lys Ile Gly Tyr Leu Leu Phe Glu Asn Met Cys Gly Val Leu Ala<br>               1195                   1200                   1205 | 3773 |
| GAG AAC AAG AGG ATT CCC GAG TTC GTC TTC ACG TCC CCG AAA GGG GTT<br>Glu Asn Lys Arg Ile Pro Glu Phe Val Phe Thr Ser Pro Lys Gly Val<br>1210                     1215                   1220 | 3821 |
| CGG CTG GCC TTC CTT GAG GGG TAC TCA TCG GCG ATG GCG ACG TCC ACC<br>Arg Leu Ala Phe Leu Glu Gly Tyr Ser Ser Ala Met Ala Thr Ser Thr<br>               1225                   1230                   1235 | 3869 |
| GAA CAA GAG ACT CAG GCT CTC AAC GAA AAG CGA GCT TTA GCG AAC CAG<br>Glu Gln Glu Thr Gln Ala Leu Asn Glu Lys Arg Ala Leu Ala Asn Gln<br>1240                     1245                   1250 | 3917 |
| CTC GTC CTC CTC TTG AAC TCG GTG GGG GTC TCT GCT GTA AAA CTT GGG<br>Leu Val Leu Leu Leu Asn Ser Val Gly Val Ser Ala Val Lys Leu Gly<br>1255                     1260                   1265                   1270 | 3965 |
| CAC GAC AGC GGC GTT TAC AGG GTC TAT ATA AAC GAG GAG CTC CCG TTC<br>His Asp Ser Gly Val Tyr Arg Val Tyr Ile Asn Glu Glu Leu Pro Phe<br>               1275                   1280                   1285 | 4013 |
| GTA AAG CTG GAC AAG AAA AAG AAC GCC TAC TAC TCA CAC GTG ATC CCC<br>Val Lys Leu Asp Lys Lys Lys Asn Ala Tyr Tyr Ser His Val Ile Pro<br>1290                     1295                   1300 | 4061 |
| AAG GAA GTC CTG AGC GAG GTC TTT GGG AAG GTT TTC CAG AAA AAC GTC<br>Lys Glu Val Leu Ser Glu Val Phe Gly Lys Val Phe Gln Lys Asn Val<br>               1305                   1310                   1315 | 4109 |
| AGT CCT CAG ACC TTC AGG AAG ATG GTC GAG GAC GGA AGA CTC GAT CCC<br>Ser Pro Gln Thr Phe Arg Lys Met Val Glu Asp Gly Arg Leu Asp Pro<br>1320                     1325                   1330 | 4157 |
| GAA AAG GCC CAG AGG CTC TCC TGG CTC ATT GAG GGG GAC GTA GTG CTC<br>Glu Lys Ala Gln Arg Leu Ser Trp Leu Ile Glu Gly Asp Val Val Leu<br>1335                     1340                   1345                   1350 | 4205 |
| GAC CGC GTT GAG TCC GTT GAT GTG GAA GAC TAC GAT GGT TAT GTC TAT<br>Asp Arg Val Glu Ser Val Asp Val Glu Asp Tyr Asp Gly Tyr Val Tyr<br>               1355                   1360                   1365 | 4253 |
| GAC CTG AGC GTC GAG GAC AAC GAG AAC TTC CTC GTT GGC TTT GGG TTG<br>Asp Leu Ser Val Glu Asp Asn Glu Asn Phe Leu Val Gly Phe Gly Leu<br>1370                     1375                   1380 | 4301 |
| GTC TAT GCT CAC AAC AGC TAC TAC GGT TAC TAC GGC TAT GCA AGG GCG<br>Val Tyr Ala His Asn Ser Tyr Tyr Gly Tyr Tyr Gly Tyr Ala Arg Ala<br>               1385                   1390                   1395 | 4349 |
| CGC TGG TAC TGC AAG GAG TGT GCA GAG AGC GTA ACG GCC TGG GGA AGG<br>Arg Trp Tyr Cys Lys Glu Cys Ala Glu Ser Val Thr Ala Trp Gly Arg<br>1400                     1405                   1410 | 4397 |
| GAG TAC ATA ACG ATG ACC ATC AAG GAG ATA GAG GAA AAG TAC GGC TTT<br>Glu Tyr Ile Thr Met Thr Ile Lys Glu Ile Glu Glu Lys Tyr Gly Phe<br>1415                     1420                   1425                   1430 | 4445 |
| AAG GTA ATC TAC AGC GAC ACC GAC GGA TTT TTT GCC ACA ATA CCT GGA<br>Lys Val Ile Tyr Ser Asp Thr Asp Gly Phe Phe Ala Thr Ile Pro Gly<br>               1435                   1440                   1445 | 4493 |
| GCC GAT GCT GAA ACC GTC AAA AAG AAG GCT ATG GAG TTC CTC AAC TAT<br>Ala Asp Ala Glu Thr Val Lys Lys Lys Ala Met Glu Phe Leu Asn Tyr<br>1450                     1455                   1460 | 4541 |
| ATC AAC GCC AAA CTT CCG GGC GCG CTT GAG CTC GAG TAC GAG GGC TTC<br>Ile Asn Ala Lys Leu Pro Gly Ala Leu Glu Leu Glu Tyr Glu Gly Phe<br>1465                     1470                   1475 | 4589 |

-continued

| | |
|---|---|
| TAC AAA CGC GGC TTC TTC GTC ACG AAG AAG AAG TAT GCG GTG ATA GAC<br>Tyr Lys Arg Gly Phe Phe Val Thr Lys Lys Lys Tyr Ala Val Ile Asp<br>              1480                     1485                  1490 | 4637 |
| GAG GAA GGC AAG ATA ACA ACG CGC GGA CTT GAG ATT GTG AGG CGT GAC<br>Glu Glu Gly Lys Ile Thr Thr Arg Gly Leu Glu Ile Val Arg Arg Asp<br>1495                     1500                     1505                 1510 | 4685 |
| TGG AGC GAG ATA GCG AAA GAG ACG CAG GCG AGG GTT CTT GAA GCT TTG<br>Trp Ser Glu Ile Ala Lys Glu Thr Gln Ala Arg Val Leu Glu Ala Leu<br>              1515                     1520                  1525 | 4733 |
| CTA AAG GAC GGT GAC GTC GAG AAG GCC GTG AGG ATA GTC AAA GAA GTT<br>Leu Lys Asp Gly Asp Val Glu Lys Ala Val Arg Ile Val Lys Glu Val<br>                  1530                     1535                  1540 | 4781 |
| ACC GAA AAG CTG AGC AAG TAC GAG GTT CCG CCG GAG AAG CTG GTG ATC<br>Thr Glu Lys Leu Ser Lys Tyr Glu Val Pro Pro Glu Lys Leu Val Ile<br>            1545                     1550                     1555 | 4829 |
| CAC GAG CAG ATA ACG AGG GAT TTA AAG GAC TAC AAG GCA ACC GGT CCC<br>His Glu Gln Ile Thr Arg Asp Leu Lys Asp Tyr Lys Ala Thr Gly Pro<br>                1560                     1565                  1570 | 4877 |
| CAC GTT GCC GTT GCC AAG AGG TTG GCC GCG AGA GGA GTC AAA ATA CGC<br>His Val Ala Val Ala Lys Arg Leu Ala Ala Arg Gly Val Lys Ile Art<br>1575                     1580                     1585                 1590 | 4925 |
| CCT GGA ACG GTG ATA AGC TAC ATC GTG CTC AAG GGC TCT GGG AGG ATA<br>Pro Gly Thr Val Ile Ser Tyr Ile Val Leu Lys Gly Ser Gly Arg Ile<br>              1595                     1600                  1605 | 4973 |
| GGC GAC AGG GCG ATA CCG TTC GAC GAG TTC GAC CCG ACG AAG CAC AAG<br>Gly Asp Arg Ala Ile Pro Phe Asp Glu Phe Asp Pro Thr Lys His Lys<br>                1610                     1615                  1620 | 5021 |
| TAC GAC GCC GAG TAC TAC ATT GAG AAC CAG GTT CTC CCA GCC GTT GAG<br>Tyr Asp Ala Glu Tyr Tyr Ile Glu Asn Gln Val Leu Pro Ala Val Glu<br>            1625                     1630                     1635 | 5069 |
| AGA ATT CTG AGA GCC TTC GGT TAC CGC AAG GAA GAC CTG CGC TAC CAG<br>Arg Ile Leu Arg Ala Phe Gly Tyr Arg Lys Glu Asp Leu Arg Tyr Gln<br>        1640                     1645                     1650 | 5117 |
| AAG ACG AGA CAG GTT GGT TTG AGT GCT TGG CTG AAG CCG AAG GGA ACT<br>Lys Thr Arg Gln Val Gly Leu Ser Ala Trp Leu Lys Pro Lys Gly Thr<br>1655                     1660                     1665                 1670 | 5165 |
| TGACCTTTCC ATTTGTTTTC CAGCGGATAA CCCTTTAACT TCCCTTTCAA AAACTCCCTT | 5225 |
| TAGGGAAAGA CCATGAAGAT AGAAATCCGG CGGCGCCCGG TTAAATACGC TAGGATAGAA | 5285 |
| GTGAAGCCAG ACGGCAGGGT AGTCGTCACT GCCCCGAGGG TTCAACGTTG AGAAGTT | 5342 |

(2) INFORMATION FOR SEQ ID NO:2:

(i) SEQUENCE CHARACTERISTICS:
        (A) LENGTH:774 amino acids
        (B) TYPE: amino acid
        (D) TOPOLOGY: linear (ii) MOLECULE TYPE: protein (xi) SEQUENCE DESCRIPTION: SEQ ID NO:2:

Met Ile Leu Asp Thr Asp Tyr Ile Thr Glu Asp Gly Lys Pro Val Ile
               5                       10                      15

Arg Ile Phe Lys Lys Glu Asn Gly Glu Phe Lys Ile Glu Tyr Asp Arg
              20                      25                      30

Thr Phe Glu Pro Tyr Phe Tyr Ala Leu Leu Lys Asp Asp Ser Ala Ile
        35                      40                      45

Glu Glu Val Lys Lys Ile Thr Ala Glu Arg His Gly Thr Val Val Thr
     50                      55                      60

Val Lys Arg Val Glu Lys Val Gln Lys Lys Phe Leu Gly Arg Pro Val
 65                  70                      75                      80

-continued

```
Glu Val Trp Lys Leu Tyr Phe Thr His Pro Gln Asp Val Pro Ala Ile
                 85                  90                  95
Arg Asp Lys Ile Arg Glu His Gly Ala Val Ile Asp Ile Tyr Glu Tyr
                100                 105                 110
Asp Ile Pro Phe Ala Lys Arg Tyr Leu Ile Asp Lys Gly Leu Val Pro
                115                 120                 125
Met Glu Gly Asp Glu Leu Lys Met Leu Ala Phe Asp Ile Glu Thr
130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
                180                 185                 190
Arg Phe Leu Arg Val Val Lys Glu Lys Asp Pro Asp Val Leu Ile Thr
                195                 200                 205
Tyr Asn Gly Asp Asn Phe Asp Phe Ala Tyr Leu Lys Lys Arg Cys Glu
                210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Gln Pro Lys Glu
                275                 280                 285
Lys Val Tyr Ala Glu Glu Ile Thr Pro Ala Trp Glu Thr Gly Glu Asn
290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Lys Glu Leu Ala Arg Arg Arg Gln Ser Tyr
                370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Ile Lys
                450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
```

```
                    500             505             510
Val Thr Ala Trp Gly Arg Glu Tyr Ile Thr Met Thr Ile Lys Glu Ile
            515             520             525

Glu Glu Lys Tyr Gly Phe Lys Val Ile Tyr Ser Asp Thr Asp Gly Phe
    530             535             540

Phe Ala Thr Ile Pro Gly Ala Asp Ala Glu Thr Val Lys Lys Lys Ala
545             550             555             560

Met Glu Phe Leu Asn Tyr Ile Asn Ala Lys Leu Pro Gly Ala Leu Glu
                565             570             575

Leu Glu Tyr Glu Gly Phe Tyr Arg Gly Phe Phe Val Thr Lys Lys
            580             585             590

Lys Tyr Ala Val Ile Asp Glu Glu Gly Lys Ile Thr Thr Arg Gly Leu
            595             600             605

Glu Ile Val Arg Arg Asp Trp Ser Glu Ile Ala Lys Glu Thr Gln Ala
610             615             620

Arg Val Leu Glu Ala Leu Leu Lys Asp Gly Asp Val Glu Lys Ala Val
625             630             635             640

Arg Ile Val Lys Glu Val Thr Glu Lys Leu Ser Lys Tyr Glu Val Pro
                645             650             655

Pro Glu Lys Leu Val Ile His Glu Gln Ile Thr Arg Asp Leu Lys Asp
                660             665             670

Tyr Lys Ala Thr Gly Pro His Val Ala Val Ala Lys Arg Leu Ala Ala
            675             680             685

Arg Gly Val Lys Ile Arg Pro Gly Thr Val Ile Ser Tyr Ile Val Leu
            690             695             700

Lys Gly Ser Gly Arg Ile Gly Asp Arg Ala Ile Pro Phe Asp Glu Phe
705             710             715             720

Asp Pro Thr Lys His Lys Tyr Asp Ala Glu Tyr Tyr Ile Glu Asn Gln
                725             730             735

Val Leu Pro Ala Val Glu Arg Ile Leu Arg Ala Phe Gly Tyr Arg Lys
                740             745             750

Glu Asp Leu Arg Tyr Gln Lys Thr Arg Gln Val Gly Leu Ser Ala Trp
            755             760             765

Leu Lys Pro Lys Gly Thr
770
```

(2) INFORMATION FOR SEQ ID NO:3:

(i) SEQUENCE CHARACTERISTICS:
        (A) LENGTH: 2325 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:3:

```
ATGATCCTCG ACACTGACTA CATAACCGAG GATGGAAAGC CTGTCATAAG AATTTTCAAG      60

AAGGAAAACG GCGAGTTTAA GATTGAGTAC GACCGGACTT TGAACCCTA CTTCTACGCC      120

CTCCTGAAGG ACGATTCTGC CATTGAGGAA GTCAAGAAGA TAACCGCCGA GAGGCACGGG     180

ACGGTTGTAA CGGTTAAGCG GGTTGAAAAG GTTCAGAAGA AGTTCCTCGG AGACCAGTT      240

GAGGTCTGGA AACTCTACTT TACTCATCCG CAGGACGTCC CAGCGATAAG GGACAAGATA     300

CGAGAGCATG GAGCAGTTAT TGACATCTAC GAGTACGACA TACCCTTCGC CAAGCGCTAC     360

CTCATAGACA AGGGATTAGT GCCAATGGAA GGCGACGAGG AGCTGAAAAT GCTCGCCTTC     420
```

-continued

```
GACATTGAAA CTCTCTACCA TGAGGGCGAG GAGTTCGCCG AGGGGCCAAT CCTTATGATA      480

AGCTACGCCG ACGAGGAAGG GGCCAGGGTG ATAACTTGGA AGAACGTGGA TCTCCCCTAC      540

GTTGACGTCG TCTCGACGGA GAGGGAGATG ATAAAGCGCT TCCTCCGTGT TGTGAAGGAG      600

AAAGACCCGG ACGTTCTCAT AACCTACAAC GGCGACAACT TCGACTTCGC CTATCTGAAA      660

AAGCGCTGTG AAAAGCTCGG AATAAACTTC GCCCTCGGAA GGGATGGAAG CGAGCCGAAG      720

ATTCAGAGGA TGGGCGACAG GTTTGCCGTC GAAGTGAAGG GACGGATACA CTTCGATCTC      780

TATCCTGTGA TAAGCGGAC GATAAACCTG CCCACATACA CGCTTGAGGC CGTTTATGAA       840

GCCGTCTTCG GTCAGCCGAA GGAGAAGGTT TACGCTGAGG AAATAACACC AGCCTGGGAA      900

ACCGGCGAGA ACCTTGAGAG AGTCGCCCGC TACTCGATGG AAGATGCGAA GGTCACATAC      960

GAGCTTGGGA AGGAGTTCCT TCCGATGGAG CCCAGCTTT CTCGCTTAAT CGGCCAGTCC      1020

CTCTGGGACG TCTCCCGCTC CAGCACTGGC AACCTCGTTG AGTGGTTCCT CCTCAGGAAG     1080

GCCTATGAGA GGAATGAGCT GGCCCCGAAC AAGCCCGATG AAAAGGAGCT GGCCAGAAGA     1140

CGGCAGAGCT ATGAAGGAGG CTATGTAAAA GAGCCCGAGA GAGGGTTGTG GGAGAACATA     1200

GTGTACCTAG ATTTTAGATC CCTGTACCCC TCAATCATCA TCACCCACAA CGTCTCGCCG     1260

GATACGCTCA ACAGAGAAGG ATGCAAGGAA TATGACGTTG CCCCACAGGT CGGCCACCGC     1320

TTCTGCAAGG ACTTCCCAGG ATTTATCCCG AGCCTGCTTG GAGACCTCCT AGAGGAGAGG     1380

CAGAAGATAA AGAAGAAGAT GAAGGCCACG ATTGACCCGA TCGAGAGGAA GCTCCTCGAT     1440

TACAGGCAGA GGGCCATCAA GATCCTGGCA ACAGCTACT ACGGTTACTA CGGCTATGCA      1500

AGGGCGCGCT GGTACTGCAA GGAGTGTGCA GAGAGCGTAA CGGCCTGGGG AAGGGAGTAC     1560

ATAACGATGA CCATCAAGGA GATAGAGGAA AAGTACGGCT TTAAGGTAAT CTACAGCGAC     1620

ACCGACGGAT TTTTTGCCAC AATACCTGGA GCCGATGCTG AAACCGTCAA AAAGAAGGCT     1680

ATGGAGTTCC TCAACTATAT CAACGCCAAA CTTCCGGGCG CGCTTGAGCT CGAGTACGAG     1740

GGCTTCTACA AACGCGGCTT CTTCGTCACG AAGAAGAAGT ATGCGGTGAT AGACGAGGAA     1800

GGCAAGATAA CAACGCGCGG ACTTGAGATT GTGAGGCGTG ACTGGAGCGA GATAGCGAAA     1860

GAGACGCAGG CGAGGGTTCT TGAAGCTTTG CTAAAGGACG GTGACGTCGA GAAGGCCGTG     1920

AGGATAGTCA AAGAAGTTAC CGAAAAGCTG AGCAAGTACG AGGTTCCGCC GGAGAAGCTG     1980

GTGATCCACG AGCAGATAAC GAGGGATTTA AAGGACTACA AGGCAACCGG TCCCCACGTT     2040

GCCGTTGCCA AGAGGTTGGC CGCGAGAGGA GTCAAAATAC GCCCTGGAAC GGTGATAAGC     2100

TACATCGTGC TCAAGGGCTC TGGGAGGATA GGCGACAGGG CGATACCGTT CGACGAGTTC     2160

GACCCGACGA AGCACAAGTA CGACGCCGAG TACTACATTG AGAACCAGGT TCTCCCAGCC     2220

GTTGAGAGAA TTCTGAGAGC CTTCGGTTAC CGCAAGGAAG ACCTGCGCTA CCAGAAGACG     2280

AGACAGGTTG GTTTGAGTGC TTGGCTGAAG CCGAAGGGAA CTTGA                     2325
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
CTTTTGCTCA GATCTTCTTT CCTG                                             24
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CAGGAAAGAA GATCTGAGCA AAAG                                      24
```

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CTGAAAATGC TCGCCTTCGC GATTGCAACT CTCTAC                         36
```

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
CTGAAAATGC TCGCCTTCGC GATTGAAACT CTCT                           34
```

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GCCCTCGTGG TAGAGAGTTG CAATGTCGAA                                30
```

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
CGGACGTACT GATAACGTAC GACGGTGACA AC                             32
```

(2) INFORMATION FOR SEQ ID NO:10:

(i) SEQUENCE CHARACTERISTICS:
        (A) LENGTH: 32 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:10:

CGGACGTACT GATAACGTAC GACGGTGACA AC                                         32

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TGGCTAGCCA AGGAACCACC AGTTGATTAG CAGAG                                      35

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATAAGAGGTC CCAAGACTTA GTACCTGAAG GGTGA                                      35

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

AAAAAGTACT CACCAGTCAC AGAAAAGCAT CTTAC                                      35

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AAAAAGTACT CAACCAAGTC ATTCCTGAGA ATAGT                                      35

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:15:

CGCCAGGGTT TTCCCAGTCA CGAC                                          24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CTTTTGCTCA GATCTTCTTT CCTG                                          24

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AGCTGAAAAT GCTAGCCTTC GACAATGAAA CTCTCT                             36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGCTGAAAAT GCTAGCCTTC GACGAAGAAA CTCTCT                             36

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GAAAATGCTC GCCTTTGATC AAGAAACTCT CTA                                33

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AGCTGAAAAT GCTAGCCTTC GACGATGAAA CTCTCT                             36

(2) INFORMATION FOR SEQ ID NO:21:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:21:

CGCCTTCGAC ATTGAAGTAC TCTACCATGA                    30

(2) INFORMATION FOR SEQ ID NO:22:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:22:

AGCTGAAAAT GCTAGCCTTC GACAGAGAAA CTCTCT              36

(2) INFORMATION FOR SEQ ID NO:23:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:23:

AGCTGAAAAT GCTAGCCTTC GACAAAGAAA CTCTCT              36